(12) United States Patent
Rafiee et al.

(10) Patent No.: US 8,454,683 B2
(45) Date of Patent: Jun. 4, 2013

(54) ANNULOPLASTY DEVICE HAVING A HELICAL ANCHOR AND METHODS FOR ITS USE

(75) Inventors: Nasser Rafiee, Andover, MA (US); Nareak Douk, Lowell, MA (US); Eliot Bloom, Hopkinton, NH (US); Michael Finney, Beverly, MA (US); Morgan House, Newfields, NH (US); Rany Huynh, Charlestown, MA (US); Stuart Mac Donald, Haverhill, MA (US); Juan-Pablo Mas, Somerville, MA (US); David Barone, Lexington, MA (US)

(73) Assignee: Medtronic Vascular, Inc., Santa Rosa, CA (US)

( * ) Notice: Subject to any disclaimer, the term of this patent is extended or adjusted under 35 U.S.C. 154(b) by 893 days.

(21) Appl. No.: 11/734,536

(22) Filed: Apr. 12, 2007

(65) Prior Publication Data

US 2007/0244553 A1    Oct. 18, 2007

Related U.S. Application Data

(60) Provisional application No. 60/791,553, filed on Apr. 12, 2006, provisional application No. 60/791,340, filed on Apr. 12, 2006, provisional application No. 60/793,879, filed on Apr. 21, 2006.

(51) Int. Cl.
*A61F 2/24* (2006.01)
(52) U.S. Cl.
USPC ........................................................ 623/2.11
(58) Field of Classification Search
USPC ..................................... 623/2.11, 2.36, 2.37
See application file for complete search history.

(56) References Cited

U.S. PATENT DOCUMENTS

| | | | |
|---|---|---|---|
| 5,545,148 A | 8/1996 | Wurster |
| 5,582,616 A | 12/1996 | Bolduc et al. |
| 5,669,919 A | 9/1997 | Sanders et al. |
| 5,682,906 A | 11/1997 | Sterman et al. |
| 5,810,882 A | 9/1998 | Bolduc et al. |
| 5,891,159 A | 4/1999 | Sherman et al. |
| 5,935,138 A | 8/1999 | McJames, II et al. |
| 5,972,020 A | 10/1999 | Carpentier et al. |
| 6,159,240 A | 12/2000 | Sparer et al. |
| 6,182,664 B1 | 2/2001 | Cosgrove |
| 6,250,308 B1 | 6/2001 | Cox |
| 6,258,069 B1 | 7/2001 | Carpentier et al. |
| 6,514,263 B1 | 2/2003 | Stefanchik et al. |
| 6,524,338 B1 | 2/2003 | Gundry |
| 6,562,051 B1 | 5/2003 | Bolduc et al. |

(Continued)

FOREIGN PATENT DOCUMENTS

| | | |
|---|---|---|
| WO | WO01/00114 | 1/2001 |
| WO | WO02/062263 | 8/2002 |

(Continued)

*Primary Examiner* — Gregory Anderson

(57) ABSTRACT

A system for modifying a heart valve annulus includes a helically helical anchored annuloplasty device delivered to the annulus via an elongated delivery member. The helical anchors of the devices disclosed herein are rotated into the valve annulus along an anchor guide by using a driver that is movably disposed in the delivery member. A tether is disposed within an inner channel of the helical anchor and a locking device is used to secure the annuloplasty device after the valve annulus has been modified. The annuloplasty device can be delivered to the annulus using, traditional surgical approach or a minimally invasive or catheter based methods.

15 Claims, 27 Drawing Sheets

U.S. PATENT DOCUMENTS

| | | |
|---|---|---|
| 6,619,291 B2 | 9/2003 | Hlavka et al. |
| 6,626,917 B1 | 9/2003 | Craig |
| 6,663,633 B1 | 12/2003 | Pierson, III |
| 6,689,164 B1 | 2/2004 | Seguin |
| 6,702,826 B2 | 3/2004 | Liddicoat et al. |
| 6,840,246 B2 | 1/2005 | Downing |
| 6,884,248 B2 | 4/2005 | Bolduc et al. |
| 6,902,570 B2 | 6/2005 | Schraft et al. |
| 7,118,595 B2 | 10/2006 | Ryan et al. |
| 7,175,659 B2 | 2/2007 | Hill et al. |
| 7,588,582 B2 * | 9/2009 | Starksen et al. ............ 606/139 |
| 7,666,193 B2 * | 2/2010 | Starksen et al. ............ 606/142 |
| 2002/0156526 A1 | 10/2002 | Hlavka et al. |
| 2002/0161378 A1 | 10/2002 | Downing |
| 2003/0176917 A1 | 9/2003 | Ryan et al. |
| 2003/0220685 A1 | 11/2003 | Hlavka et al. |
| 2004/0024414 A1 | 2/2004 | Downing |
| 2004/0153147 A1 | 8/2004 | Mathis |
| 2004/0236419 A1 | 11/2004 | Milo |
| 2005/0027352 A1 | 2/2005 | Cosgrove et al. |
| 2005/0049698 A1 | 3/2005 | Bolling et al. |
| 2005/0065601 A1 | 3/2005 | Lee et al. |
| 2005/0075659 A1 | 4/2005 | Realyvasquez et al. |
| 2005/0131533 A1 | 6/2005 | Alfieri et al. |
| 2005/0171601 A1 | 8/2005 | Cosgrove et al. |
| 2005/0177180 A1 | 8/2005 | Kaganov et al. |
| 2007/0027533 A1 | 2/2007 | Douk |
| 2007/0051377 A1 | 3/2007 | Douk et al. |
| 2007/0083259 A1 | 4/2007 | Bloom et al. |

FOREIGN PATENT DOCUMENTS

| | | |
|---|---|---|
| WO | WO03/105667 | 12/2003 |
| WO | WO2004/045463 | 6/2004 |
| WO | WO2004/112585 | 12/2004 |
| WO | WO2005/025644 | 3/2005 |
| WO | WO2005/046488 | 5/2005 |
| WO | WO2005/058206 | 6/2005 |

* cited by examiner

ANNULOPLASTY DEVICE HAVING A HELICAL ANCHOR AND METHODS FOR ITS USE

CROSS-REFERENCE TO RELATED APPLICATION

The present application claims priority to U.S. Provisional Application 60/791,553, filed Apr. 12, 2006 and titled "Annuloplasty Device Having Helical anchors"; U.S. Provisional Application No. 60/791,340, filed Apr. 12, 2006 and titled "Minimally Invasive Procedure for Implanting an Annuloplasty Device"; and U.S. Provisional Application 60/793,879, filed Apr. 21, 2006 and titled "Annuloplasty Device Having Helical anchors", of which the entire contents of each are incorporated herein by reference.

FIELD OF INVENTION

This invention relates generally to the treatment of heart valves and particularly to systems, devices and methods for treating valvular regurgitation by increasing leaflet coaption.

BACKGROUND

The heart is a four-chambered pump that moves blood efficiently through the vascular system. Blood enters the heart through the vena cava and flows into the right atrium. From the right atrium, blood flows through the tricuspid valve and into the right ventricle, which then contracts and forces blood through the pulmonic valve and into the lungs. Oxygenated blood returns from the lungs and enters the heart through the left atrium and passes through the mitral valve into the left ventricle. The left ventricle contracts and pumps blood through the aortic valve into the aorta and to the vascular system.

The mitral valve consists of two leaflets (anterior and posterior) attached to a fibrous ring or annulus. In a healthy heart, the mitral valve leaflets close during contraction of the left ventricle and prevent blood from flowing back into the left atrium. Due to various cardiac diseases, however, the mitral valve annulus may become distended causing the leaflets to remain partially open during ventricular contraction and thus allow regurgitation of blood into the left atrium. This results in reduced ejection volume from the left ventricle, causing the left ventricle to compensate with a larger stroke volume. However, the increased workload eventually results in dilation and hypertrophy of the left ventricle, further enlarging and distorting the shape of the mitral valve. If left untreated, the condition may result in cardiac insufficiency, ventricular failure, and ultimately death.

It is common medical practice to treat mitral valve regurgitation by either valve replacement or repair. Mitral valve repair includes a variety of procedures to repair or reshape the leaflets to improve closure of the valve during ventricular contraction. If the mitral valve annulus has become distended, a frequent repair procedure involves implanting an annuloplasty ring on the mitral valve annulus. The annuloplasty ring generally has a smaller diameter than the annulus, and when sutured to the annulus the annuloplasty ring draws the annulus into a smaller configuration, bringing the mitral valve leaflets closer together, and allowing improved closure during ventricular contraction. Annuloplasty rings may be rigid, flexible or a combination, having both rigid and flexible segments. Rigid annuloplasty rings have the disadvantage of causing the mitral valve annulus to be rigid and unable to flex in response to the contractions of the ventricle, thus inhibiting the normal, three-dimensional movement of the mitral valve that is required for it to function optimally. Flexible annuloplasty rings are frequently made of Dacron® fabric and must be sewn to the annular ring with a line of sutures. This eventually leads to scar tissue formation and loss of flexibility and function of the mitral valve. Similarly, combination rings must generally be sutured in place and also cause scar tissue formation and loss of mitral valve flexibility and function.

Valve replacement involves an open-heart surgical procedure in which the patient's mitral valve is removed and replaced with an artificial valve. One drawback to open heart surgical techniques requires heart bypass procedures to accomplish the replacement and/or repair of the valve. Another drawback is that the open-heart procedures require that the patient undergo general anesthesia for a prolonged periods of time.

To overcome many of the complications and risks of open-heart surgical procedures, less invasive or minimally invasive surgical techniques have been developed. These procedures can be done on a beating heart and often are performed without general anesthesia or a reduced time under general anesthesia.

It would be desirable, therefore to provide a method and device for reducing valvular regurgitation that would overcome the limitations and disadvantages inherent in the devices described above.

SUMMARY OF THE INVENTION

One aspect of the invention provides a system for modifying a heart valve annulus. The system comprises an elongated generally tubular delivery member, an elongated driver movably received in the delivery member, an anchor guide, a helical anchor disposed in the delivery member, and an elongated flexible tether. The system further includes a locking device. The driver is rotatably and axially movable within the delivery member to drive the helical anchor through the annulus along the anchor guide, and wherein the tether is disposed in a pathway of the helical anchor.

One aspect of the invention provides an embodiment of the invention in which the anchor guide permanently extends from the distal end of the delivery member. Another aspect of the invention provides an embodiment of the invention in which the driver is also a generally tubular member and the anchor guide movable between a delivery position within the driver and a deployment position on the exterior of the driver.

Another aspect of the invention provides a system for modifying a heart valve annulus. The system comprises a plurality of delivery members, a plurality of helical anchors, a plurality of anchor guides, a plurality of rotatable drives for rotatably driving the helical anchors along the guides, and a single elongated flexible tether.

Another aspect of the invention provides a device for modifying the shape of a heart valve. The device comprises at least on elongated helical anchor having a sharpened portion on the distal end thereof and a plurality of coils defining an inner channel. The device further comprises a tether that is positioned within the inner channel of the helical anchor, and a locking device for securing the tether when a desired degree of modification has been achieved.

Another aspect of the invention provides a method for modifying a heart valve. The method comprises delivering an anchor guide and a helical anchor to a target valve via a delivery member, positioning the anchor guide adjacent an annulus of the valve, rotating a driver and threading the helical anchor through the annulus along the anchor guide based on the rotation of the driver.

The present invention is illustrated by the accompanying drawings and the detailed description given below. The drawings should not be taken to limit the invention to the specific embodiments, but are for explanation and understanding. The detailed description and drawings are merely illustrative of the invention rather than limiting, the scope of the invention being defined by the appended claims and equivalents thereof. The drawings are not to scale. The foregoing aspects and other attendant advantages of the present invention will become more readily appreciated by the detailed description taken in conjunction with the accompanying drawings.

DETAILED DESCRIPTION

The invention will now be described by reference to the figures wherein like numbers refer to like structures. The terms "distal" and "proximal" are used herein with reference to the treating clinician during the use of the catheter system; "Distal" indicates an apparatus portion distant from, or a direction away from the clinician and "proximal" indicates an apparatus portion near to, or a direction towards the clinician. Additionally, the term "annuloplasty" is used herein to mean modification/reconstruction of a defective heart valve.

The current invention discloses devices and methods for treating regurgitation in cardiac valves. While these devices and methods are described below in terms of being used to treat mitral regurgitation, it will be apparent to those skilled in the art that the devices could be used on other cardiac valves also. Annuloplasty devices of the current invention comprise helical anchors, tethers, and locks and they are used to modify the shape of heart valves for treating valvular regurgitation. The systems of the current invention comprised the annuloplasty devices and the delivery members for placing the devices adjacent a heart valve annulus.

Figure 1:
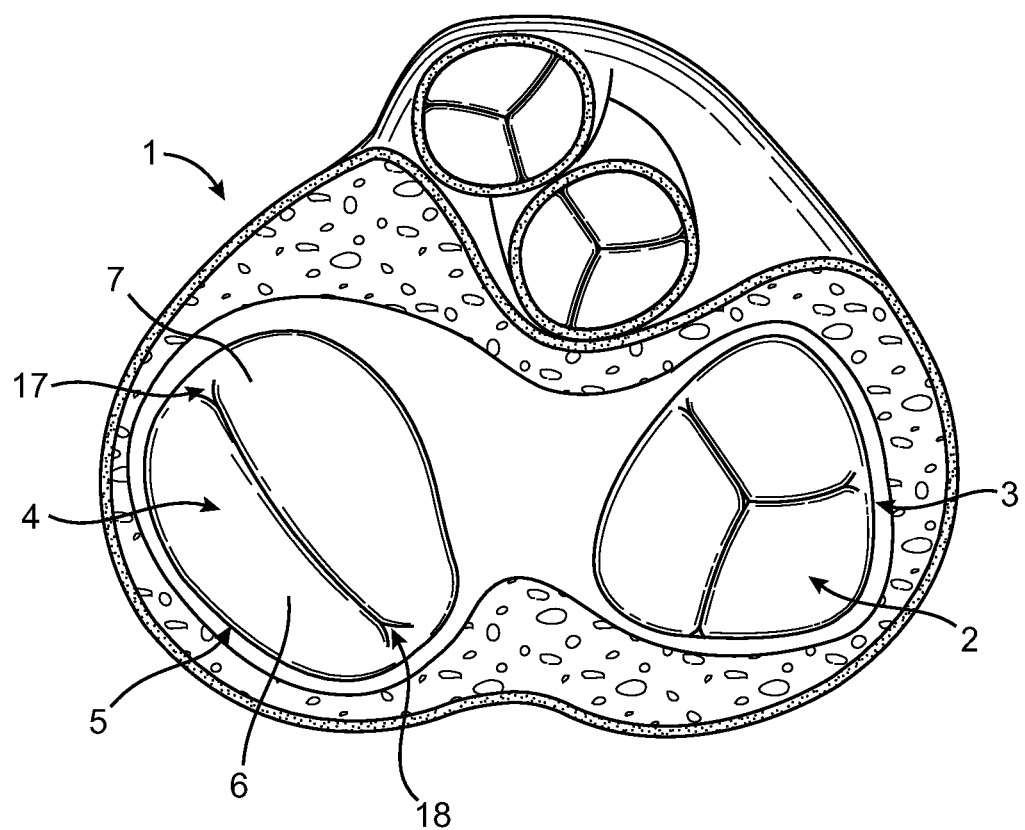
FIG. 1 is a cross-sectional schematic view of a heart showing the location of the heart valves.

Referring to the drawings, FIG. 1 shows a schematic cross-sectional view of a heart 1 having tricuspid valve 2 and tricuspid valve annulus 3. Mitral valve 4 is adjacent mitral valve annulus 5. Mitral valve 4 is a bicuspid valve having anterior cusp 7 and posterior cusp 6. Anterior cusp 7 and posterior cusp 6 are often referred to, respectively, as the anterior and posterior leaflets. Also shown in the figure are the posterior commisure 17 and the anterior commisure 18.

The devices of the current invention can be delivered to, and implanted in, a beating heart using a minimally invasive surgical technique or via catheter based delivery through the vascular system. Where devices are delivered using minimally invasive surgical procedures, the delivery instruments can be inserted through the wall of the atrium at a location directly adjacent to the posterior commisure. If the devices are delivered to the atrium via catheter, the catheter can enter the atrium through an opening created in the septal wall between the left and right atrium. The devices of the invention can also be implanted in the valves of a temporarily stopped heart and in one embodiment the device is delivered via open heart surgery.

Figure 2A:
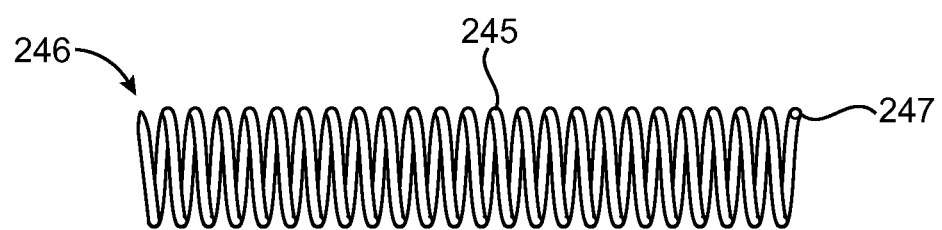
FIGS. 2A and 2B illustrate a helical anchor for an annuloplasty device according to the current invention.

FIGS. 2A through 4 illustrate the components of an embodiment of an annulus modification system for modifying a heart valve according to the current invention. Referring first to FIGS. 2A and 2B, there is shown a helical anchor for an annuloplasty device according to the current invention. As shown in FIG. 2A, helical anchor 245 comprises an elongate coiled member having a tissue penetrating tip 246 at a distal end and a proximal end 247 that is operably connected to a helical anchor driver.

The coils of the helical anchor 245 define a structure having a generally circular shape, and the tip 246 extends on a tangent away from the circular perimeter of the helical anchor. Angling the sharpened tip away from the exterior perimeter of the helical anchor makes it easier for the tip to penetrate a valve annulus when the helical anchor is being rotated out of a delivery member and along an anchor guide. In some embodiments, the length L of the sharpened tip portion is in the range of 0.045 inches to 0.065 inches. One embodiment of a helical anchor has a tip length greater than 0.065 inches, another embodiment has a tip length less than 0.045 inches, and one embodiment of a helical anchor according to the current invention has a tip length of 0.055 inches.

Helical anchor 245 comprises a biocompatible metallic or polymeric material having suitable resiliency. In one embodiment, helical anchor 245 comprises stainless steel, in anther embodiment, the helical anchor comprises 35NLT, and in yet another embodiment the helical anchor comprises MP35N. The diameter of the metallic or polymeric member that is coiled to make the helical anchor can vary based on the desired flexibility, the size of the annulus, the delivery method, etc, and some embodiments include helical anchors made from wires with diameters in a range of 0.017 inches –0.025 inches One embodiment is made from a material with a diameter smaller than 0.017 inches, another embodiment is made from a material with a diameter larger than 0.025 in, and yet another embodiment is made from a material having a diameter of 0.02 inches The coils of the helical anchor define an inner channel for a tether. Thus, the helical anchor has an outer diameter defining the exterior of the helical anchor and an inner diameter defining the channel or lumen through the helical anchor. Some embodiments of the invention include helical anchors having inner channel diameters in the range of 0.10 inches to 0.20 inches One embodiment includes a helical anchor with an inner channel diameter smaller than 0.10 inches, another embodiment has a helical anchor with an inner channel diameter larger than 0.20 inches, and yet another embodiment has a helical anchor with an inner channel diameter of 0.11 inches Outer diameters for the helical anchors are in the range of 0.150 inches to 0.250 inches One embodiment includes a helical anchor with an outer diameter smaller than 0.150 inches, another embodiment has a helical anchor with an inner diameter larger than 0.250 inches, and yet another embodiment has a helical anchor with an outer diameter of 0.150 inches.

The distance between each coil defines the coil pitch, and the pitch can also be expressed as the number of coils per inch. The number of coils per inch for the helical anchors of the current invention can vary based on the desired degree of flexibility and resiliency. Some embodiments include helical anchors having coils per inch in the range of 10 to 20. One embodiment of a helical anchor has less than 10 coils per inch, one embodiment of a helical anchor has more than 20 coils per inch, and one embodiment of a helical anchor according to the current invention has 12 coils per inch. An additional embodiment of the current invention includes helical anchors having 14 coils per inch.

In addition to the pitch, the length of the helical anchors of the various embodiments of the invention can vary based on the size of a patient's valve annulus and the number and location of helical anchors needed to modify the shape of the annulus. In one embodiment of the invention, multiple helical anchors having six coils each are implanted. In another embodiment, a single helical anchor that is 1 inch long is implanted. Some embodiments of the invention include helical anchors having a length in the range of 0.50 inches to 2.5 inches. At least one embodiment has at least one helical anchor longer than 2.5 inches and another embodiment has at least one helical anchor shorter than 0.50 inches. In at least one embodiment of the invention, helical anchors having a length in the range of 25 mm to 31 mm are implanted in the anterior portion of a mitral valve annulus. In at least one embodiment of the invention, helical anchors having a length in the range of 59 mm to 63 mm are implanted in the posterior portion of a mitral valve annulus. In another embodiment of the invention, a plurality of helical anchors having lengths in the range of 0.40 to 2.50 inches are used to alter the shape of a valve annulus. One embodiment of the invention uses a plurality of helical anchors having the same length to modify the shape of a heart valve annulus. Another embodiment of the invention uses a plurality of helical anchors where not all of the helical anchors have the same length, but some of the helical anchors have the same length.

The flexibility of the helical anchor can be controlled by the diameter of the wire or other material used to make the helical anchor and the number of coils per inch. As will be described further below a tether will be placed through the inner channel of one or more helical anchors that are implanted along a heart valve annulus. The tether will then be manipulated to exert a force on the helical anchors and modify the shape of the valve annulus. Care must be taken when choosing a helical anchor to insure that the helical anchor will be able to maintain a modified position after it has been implanted. If a helical anchor is made from a wire or other member having too large of a diameter or if a helical anchor is made with too many coils per inch, more pressure will be required to keep the helical anchor from moving to a straight elongated state. In one embodiment, the helical anchor is made from a stainless steel wire having a diameter of 0.020 inches; the helical anchor has an inner diameter of 0.110 inches and an outer diameter of 0.150 inches and a pitch of 12 coils per inch. In at least one embodiment, at least a portion of the helical anchor is made from material having a high X-ray attenuation coefficient.

Figure 2B:
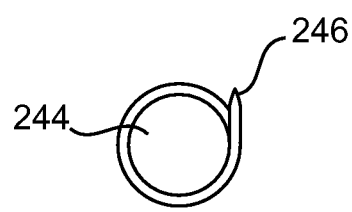

Helical anchor comprises a plurality of individual coils, and as seen in FIG. 2B, the plurality of coils form a generally cylindrical inner channel 244 that can accommodate an anchor guide and through which a portion of a tether will be disposed. In operation, the inner channel diameter, the coil pitch and the length of the tip 246 of the helical anchor may be determined to provide a specific depth of penetration of the helical anchor as it is threaded along the valve annulus.

In one embodiment (not shown), a system will include a tip sheath that can be disposed on the tip of a helical anchor. The tip sheath encases the helical anchor tip when the helical anchor is in a deployed configuration. In one embodiment, a helical anchor tip sheath includes an opening through which a tether passes.

Figure 3A:
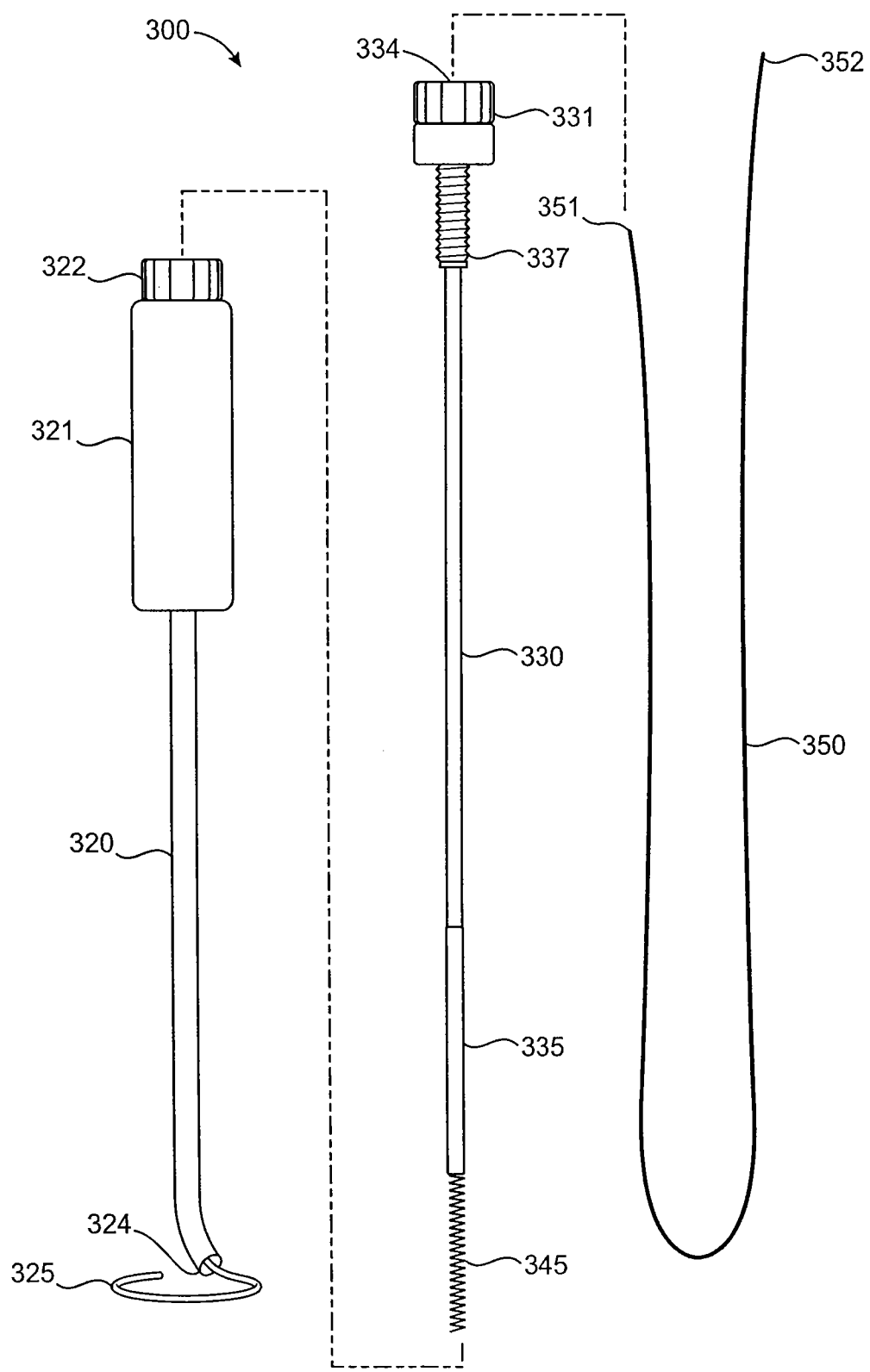
FIGS. 3A-3C illustrate a system for modifying the shape of a heart valve annulus according to the current invention.
Figure 3B:
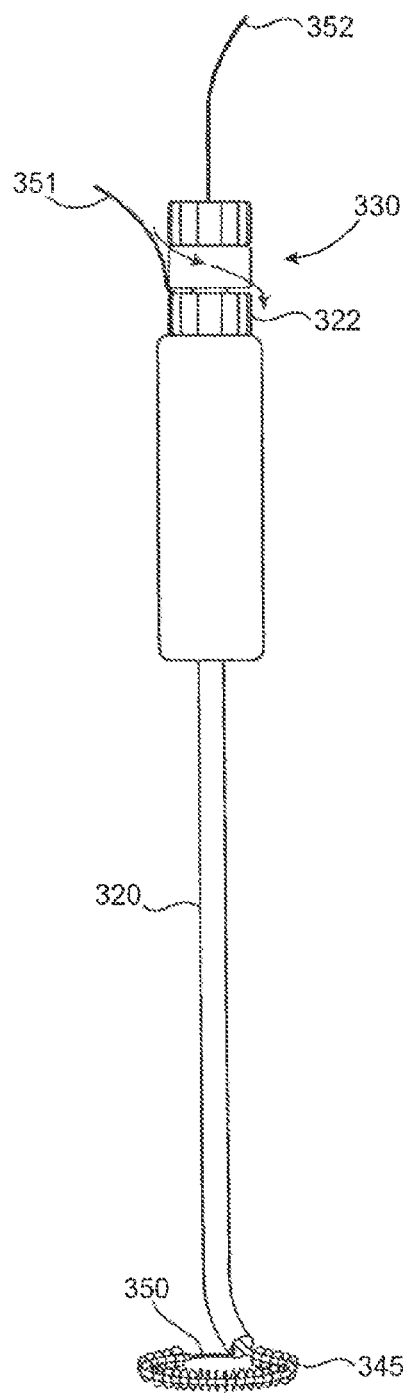
Figure 3C:
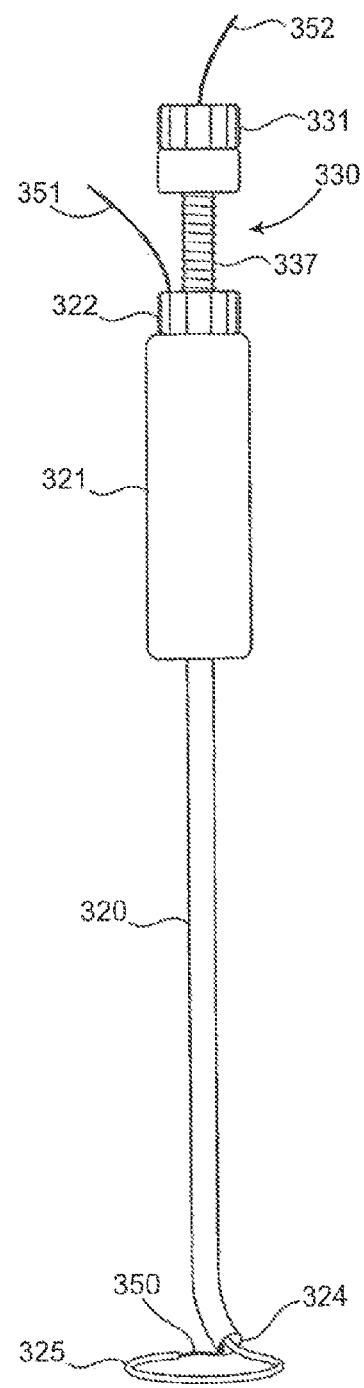

Referring now to FIGS. 3A-3C, there is shown an embodiment of a system (300 in FIG. 3A) used for a valve modification procedure where access is gained to a heart valve via a surgical approach similar to the approach currently used for implanting annuloplasty rings known in the art. While any procedure using the system depicted in FIGS. 3A through 3C does not have the advantage of being able to be performed on a beating heart (as will be described below), it does allow a clinician to modify a heart valve in less time than the devices currently available in the art allow. This will reduce the time that a patient is subjected to general anesthesia and it may promote a quicker recovery time. It will also allow a clinician to complete a valve modification procedure in a shorter period and thus allow that clinician to treat more patients.

FIG. 3A shows the elongated generally tubular delivery member 320 having a handle 321 and a handle cap 322 on the proximal end of the delivery member 320. The distal end of the delivery member 320 includes an anchor guide 325 and the distal opening 324 of the driver lumen that communicates through the length of the delivery member.

The anchor guide 325 is configured to conform to the shape of at least a portion of the valve annulus when the anchor guide is placed next to a valve annulus at the treatment site. In one embodiment of the invention, the anchor guide is configured to conform to the annulus adjacent the posterior leaflet of a mitral valve. In another embodiment of the invention, the anchor guide is configured to conform to the annulus adjacent the anterior leaflet of a mitral valve.

An elongated helical anchor driver 330 includes a driver knob 331 on the proximal end of the driver and a threaded portion 337 adjacent the knob. A distal portion 335 of the driver is connected to a helical anchor 345. The driver can be made from any biocompatible material sufficient to allow the driver to rotate and to move longitudinally inside of the delivery member, and translate the rotation and movement to the helical anchor. Most of the driver shaft can be stiff, but the distal portion 335 must be flexible to allow the driver to negotiate the curved portions near the distal end of the delivery member 320.

Figure 4:
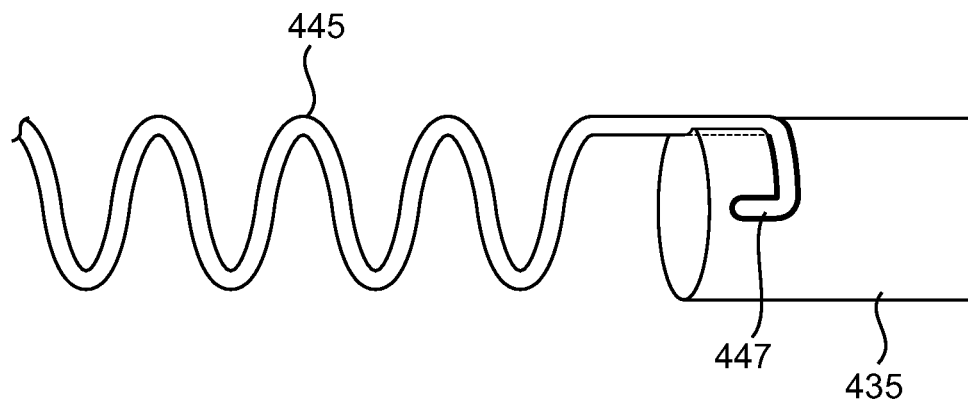
FIGS. 4 and 5 illustrate the attachment of helical anchors to an helical anchor driver according to the current invention.
Figure 5:
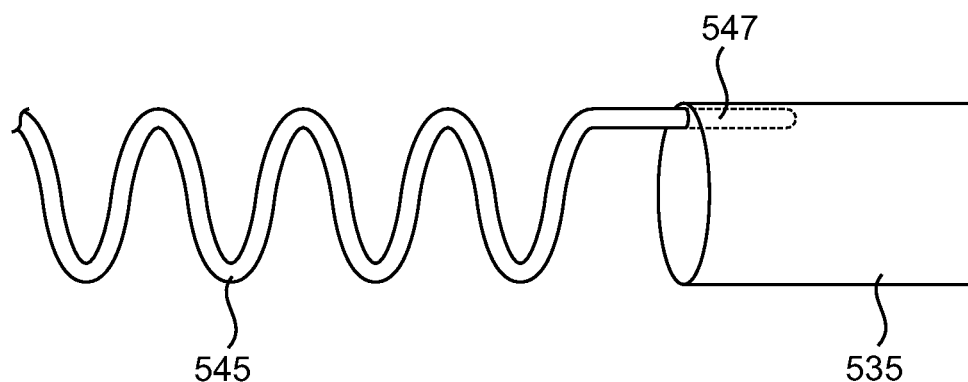

Referring to FIGS. 4 and 5, there can be seen two different embodiments of how the helical anchors of the current invention can be connected to the proximal end of the helical anchors of the current invention. FIG. 4 shows a helical anchor 445 according to the current invention wherein the helical anchor has a generally U-shaped driver portion 447 at the proximal end. The distal end 435 of the driver has an indentation in the driver's outer surface that is sized and shaped so that the driver portion at the proximal end of the helical anchor will fit snugly into the driver during delivery of the helical anchor. Once the helical anchor is implanted in a valve annulus, the driver is rotated in the opposite direction than the rotation for implanting the valve and the delivery member is manipulated so that the helical anchor separates from the driver.

FIG. 5 illustrates another embodiment of a release mechanism according to the current invention. The helical anchor 545 has a proximal end 547 with a driver portion that extends straight in a proximal direction from the helical anchor. The distal tip 535 of the driver has a hole for placement of the driver portion of the helical anchor such that the helical anchor will fit snugly into the driver during implantation. Once the helical anchor is implanted, the driver and delivery member are pulled away from the proximal end of the helical anchor and the straight driver portion of the proximal end is pulled from the hole in the distal tip of the driver. In some embodiments of the current invention, the length of the straight driver portion of the helical anchor can vary from 0.05 inches to 0.25 inches. Some embodiments of the current invention have helical anchors with straight driver portions that are longer than 0.25 inches, other embodiments of the current invention have helical anchors with straight driver portions that are shorter than 0.05 inches, and one embodiment of a helical anchor according to the current invention has a helical anchor with a straight driver portion of 0.10 inches.

In some embodiments of the current invention, the driver can be a hollow member having either a tether lumen or an anchor guide lumen communicating through its length. The helical anchor connections shown in FIGS. 4 and 5 will work equally as well for tubular driver members as they will for non-tubular driver members.

Referring again to FIG. 3A, the system also includes a flexible elongated tether 350 having a first end 351 and a second end 352. Tether 350 comprises an elongate flexible filament of biocompatible material. In one embodiment, the tether comprises a monofilament. In other embodiments the tether may comprise a braid of a plurality of filaments of the same material or of filaments from different materials. Still other embodiments of tethers comprise a braded sheath with a single filament core, or a braided sheath with a braided core. The tether 350 may be composed of biocompatible material such as, but not limited to, nylon or polyester. The tether may be constructed from material that will not stretch or it may be pre-stressed to prevent the tether from elongating after the annuloplasty devices of the current invention are implanted in a heart valve annulus. In one embodiment, the tether is made from a pre-stretched ultra-high-molecular-weight polyethylene. Various embodiments of the invention include tethers having diameters in the range of 0.015 inches and 0.050 inches in diameter. In one embodiment of the invention the tether has a diameter smaller than 0.015 inches and in another embodiment of the invention the tether has a diameter larger than 0.050 inches. One embodiment of the invention has a tether with a diameter of 0.020 inches.

The tether 350 is delivered to the treatment site in a looped configuration with first and second ends extending outside the patient's body during the implantation procedure. If additional helical anchors are desired, the ends of the tether are threaded through an additional driver, helical anchor and delivery member based on where the preceding helical anchor was implanted and where the new helical anchor will be planted relative to the preceding helical anchor.

To use the system, the first end 351 of the tether 350 is threaded into a tether lumen 334 at the proximal end of the driver and out through an inner channel of the helical anchor 345. The tether is then threaded into the driver lumen and into a tether lumen (not shown) in the anchor guide 325. The tether exits the end of the anchor guide and is routed back up through the driver lumen and exits the handle 321 through another tether lumen (not shown).

Referring to FIG. 3B, the driver 330 is inserted into the driver lumen of the delivery member 320 and advanced until the threaded portion 337 makes contact with a complementary threaded portion (not shown) on the interior of the delivery member handle 321. When the driver has been advanced to the point where the threaded portion on the driver makes contact with the threaded portion on the handle, the helical anchor 345 will be located adjacent to the anchor guide. The anchor guide 325 would then be aligned with a valve annulus and placed on the annulus in the desire location for implanting the helical anchor. Also shown in FIG. 3B are the first end 351 and the second end 352 of the tether 350; the handle cap 322 and the helical anchor 345.

Referring now to FIG. 3C, the driver knob 331 is rotated so that the threaded portion 337 on the driver is screwed into the complementary threaded portion of the delivery member 320. As the driver is threaded into the delivery member, the distal portion of the driver rotates and moves toward the distal opening 324 of the delivery member until the distal end of the helical anchor is extended from the delivery member and the distal end is rotated into and out of the valve annulus while the helical anchor is rotated along the anchor guide. Also shown in FIG. 3C are the first end 351 and the second end 352 of the tether 350; the handle 321 with handle cap 322 and the anchor guide 325. FIG. 3C further depicts driver 330.

In some embodiments of the systems of the current invention, the helical anchor is engaged to the distal tip of the driver and the driver and helical anchor are placed in the delivery member such that the anchor guide is already in the inner channel of the helical anchor. In other embodiments, the extended distal tip of the helical anchor catches the anchor guide, as the distal end of the helical anchor extends from the distal opening of the delivery member, and the helical anchor rotates itself onto and along the delivery guide as the driver is threaded into the delivery member.

Once the helical anchor is implanted, the anchor guide is either withdrawn into the delivery member or the delivery member is rotated and manipulated to remove the anchor guide from the inner channel of the helical anchor. After the anchor guide is removed from the helical anchor, a portion of the tether remains disposed in the helical anchor such that one end of the tether extends from the distal end of the helical anchor and the other end of the tether extends from the proximal end of the helical anchor.

The delivery member and driver are then withdrawn from the area of the valve annulus. The tether slides freely through the tether lumens or other portions of the delivery member and driver while they are being withdrawn, and it can be completely removed from those portions of the system such that the ends extend outside of a patient's body while a portion of the tether is disposed in the inner channel of the helical anchor implanted in the patient's heart valve annulus.

In some embodiments of the invention where additional helical anchors are desired, the delivery member and driver are withdrawn and additional delivery members and drivers are selected. The tether is threaded into tether channels or other appropriate structure of the delivery members, drivers, and helical anchors such that the helical anchors can be implanted. The tether is threaded through the additional drivers, helical anchors, and delivery members based on where the preceding helical anchor was implanted and where the new helical anchor will be planted relative to the preceding helical anchor.

In at least one embodiment where multiple helical anchors are desired, the delivery member is left inside of a patient's body and the driver is withdrawn from the delivery member. The tether is threaded into an additional helical anchor and driver. The driver is then inserted into the delivery member and advanced so that the helical anchor is at the distal opening in the delivery member. The anchor guide is then manipulated so that it is placed on the portion of the valve annulus where the additional helical anchor is desired, and the helical anchor is implanted as described above. Other additional helical anchors can be implanted using the same delivery member, or the delivery member can be withdrawn and other additional helical anchors implanted using additional delivery members and drivers as described above.

Once a desired number of helical anchors have been implanted, the clinician forms a loop out of the tether and makes the loop smaller to apply a force to the helical anchors and modify the shape of the valve annulus. When the shape of the valve annulus has reached a desired level of modification, the tether is tied using a traditional surgeons knot so that the valve annulus will be maintained in the desired state of modification. Any excess material on the tether is then trimmed away. The surgical incisions are then closed to complete the procedure.

The components of the system depicted in FIGS. 3A through 3C can be made from any suitable biocompatible material. The delivery member 320 can be made of flexible, biocompatible polymeric material such as, but not limited to, polyurethane, polyethylene, nylon and polytetrafluoroethylene (PTFE), it can be made from rigid plastics or metals such as stainless steel or other suitable metals, and it can be made from a combination of two or more of these materials.

The driver 330 can also be made from flexible, biocompatible polymeric material such as, but not limited to, polyurethane, polyethylene, nylon and polytetrafluoroethylene (PTFE). Portions of the driver can be made from rigid plastics or metals such as stainless steel of other suitable metals as long as the distal portion of the driver is made from a flexible material that will allow it to negotiated curved portions of the delivery member. In one embodiment, the proximal portion of the driver is a braided member formed from a plurality of metallic filaments. In other embodiments, the drivers can include portions made from polymeric filaments or a combination of metallic and polymeric filaments. In some embodiments of the invention, the braided portions of drivers are braided sheaths having lumens for tethers and anchor guides running therethrough.

The lumens of the delivery members and drives of the current invention can be coated with a lubricious material such as silicone, polytetrafluroethylene (PTFE), or a hydrophilic coating. The lubricious interior surface of a delivery member facilitates the longitudinal movement of a driver The anchor guide can be made from a suitable biocompatible metallic or polymeric material or combinations thereof. The anchor guides of the current invention can be made from a flexible material, but the material must be hare enough to resist penetration by the sharpened distal end of a helical anchor. In one embodiment of the invention, the anchor guide is made from stainless steel. In one embodiment of the invention, the tubular delivery member and the anchor guide are formed as a unitary piece from a biocompatible material. In other embodiments, the delivery members and anchor guides are fashioned as separate pieces that are joined together by, for example, adhesive, welding or any other manner known in the art. In another embodiment of the invention, the delivery member comprises a polymeric material and the anchor guide comprises a metal.

Figure 6A:
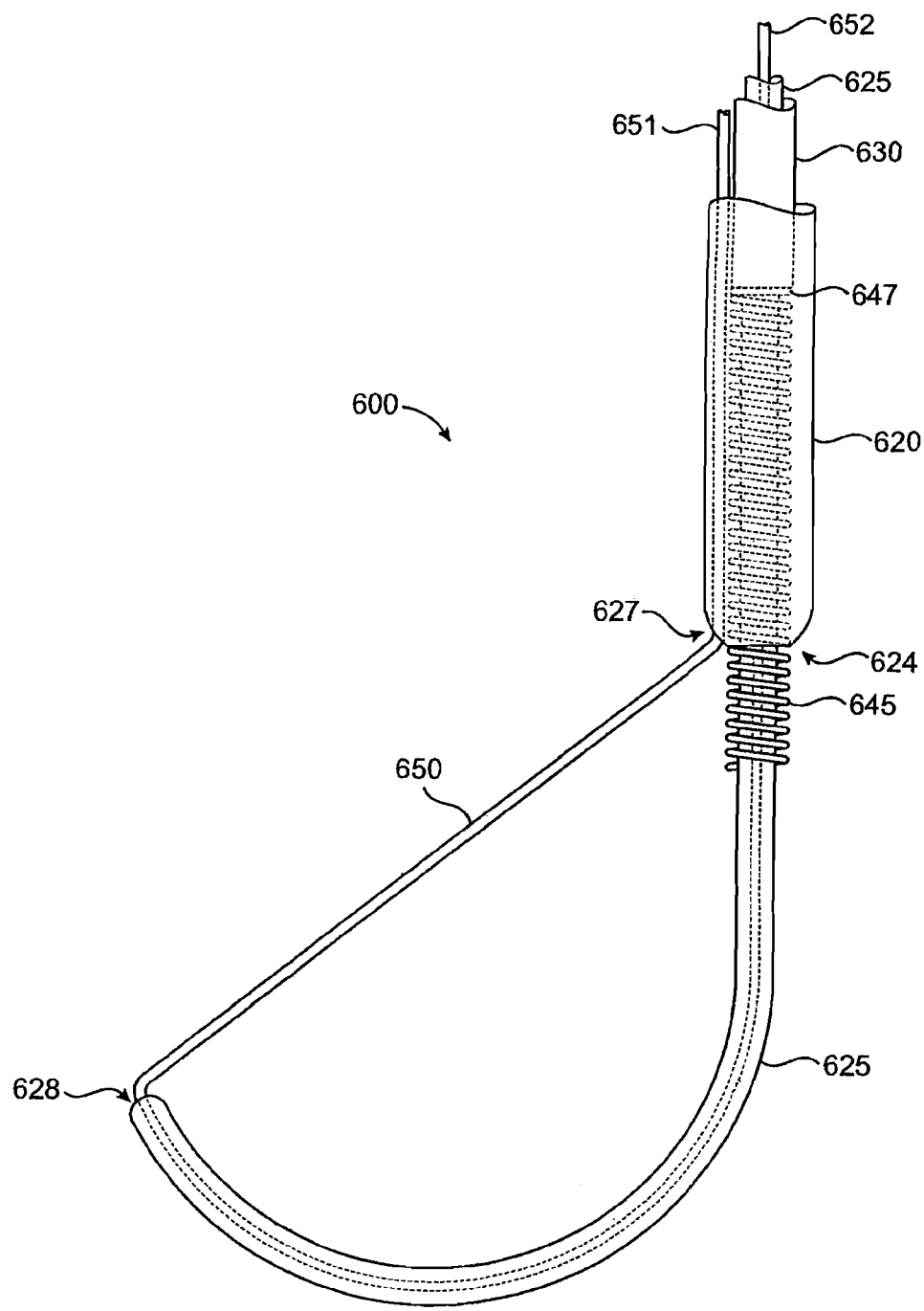
FIGS. 6A and 6B illustrate an embodiment of an annulus modification system according to the current invention.
Figure 6B:
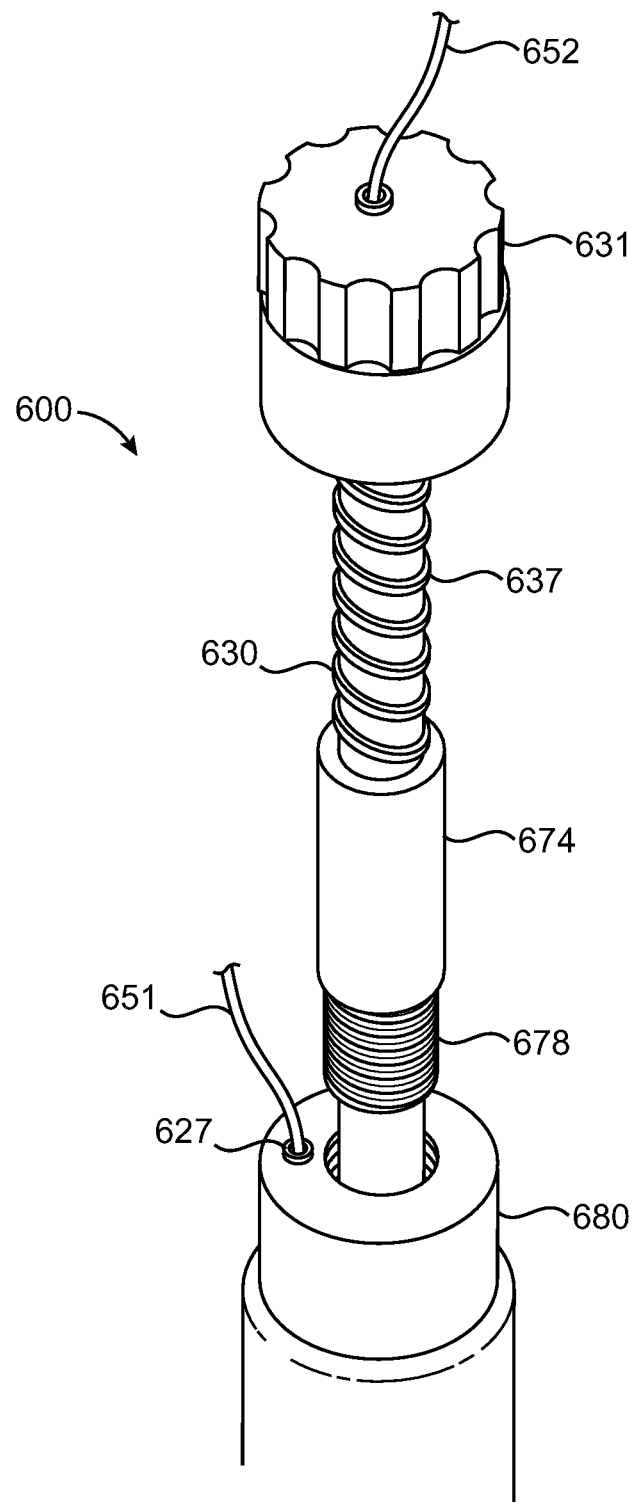

FIGS. 6A and 6B illustrate one embodiment of a catheter based annulus modification system 600, in accordance with the present invention. FIG. 6A shows the distal end of a delivery catheter of system 600. FIG. 6B illustrates the proximal end of system 600 that includes the controls for manipulating the annulus modification system.

Referring to FIG. 6A, system 600 comprises a delivery member 620, driver 630, anchor guide 625, helical anchor 645 and tether 650. The delivery member 620 comprises a flexible elongate tube for insertion into the patient. The delivery member 620 is made of flexible, biocompatible polymeric material such as, but not limited to, polyurethane, polyethylene, nylon and polytetrafluoroethylene (PTFE). The delivery member 620 includes a lumen 624 for receiving a driver 630.

The driver 630 comprises an elongate tube having a distal drive end for driving helical anchor 645. The driver is made of flexible, biocompatible polymeric material such as, but not limited to, polyurethane, polyethylene, nylon and polytetrafluoroethylene (PTFE). The driver is configured to rotatably and longitudinally translate along an axis of lumen 624 during implantation of the helical anchor. The distal end of the driver includes a helical anchor-receiving portion (not shown) for releasably holding the helical anchor. In one embodiment, the helical anchor receiving portion comprises an opening for receiving a straight portion of the proximal end 647 of the helical anchor 645. In one embodiment, the lumen 624 is coated with a lubricious material such as silicone, polytetrafluroethylene (PTFE), or a hydrophilic coating. The lubricious interior surface of the delivery member facilitates the longitudinal movement of the driver. In one embodiment, the driver includes a lumen for receiving the anchor guide 625.

The tether 650 has a first end 651 that is generally disposed in a first tether lumen 627 and a second end 652 that is generally disposed in a second tether lumen 628 located in the generally elongate anchor guide 625. The anchor guide comprises a biocompatible metallic or polymeric material or combinations thereof. Fabrication of the anchor guide may include chemical machining, forming or heat setting of nitinol. The anchor guide is configured to conform to the shape of at least a portion of the valve annulus when the anchor guide is deployed at the treatment site. In one embodiment, the anchor guide is configured to conform to the annulus adjacent the posterior leaflet. In another embodiment, the anchor guide is configured to conform to the annulus adjacent the anterior leaflet. In one embodiment of the invention, the anchor guide is constructed from a material having shape memory properties so that when the distal end of the guide it is expelled for the end of the delivery member, it assumes a curved shape that corresponds to the shape of at least a portion of a valve annulus. In another embodiment, the anchor guide is constructed from a flexible biocompatible material and it articulated into a shape corresponding to a heart valve annulus by securing one end of the tether and applying tension to the other end until the anchor guide is in a curved configuration at which time both ends of the tether are secured.

The anchor guide can have a generally circular or elliptical cross-section such that at least a portion of the exterior surface of the guide has a shape that is complementary to the radius of curvature of helical anchor. During deployment of helical anchor, the helical anchor contacts surface of the anchor guide, which guides the helical anchor as it advances along the length of anchor guide.

During the delivery of a helical anchor to a valve annulus, the various components of the system are concentrically disposed within the delivery member. Those with skill in the art will recognize that the arrangement of the various components within the delivery member may be different from that described and illustrated in the figures.

FIG. 6B illustrates the proximal end of system 600 that includes the controls for manipulating the various components of the system. The proximal end of the driver 630 includes a driver knob 631, a threaded portion 637 and a lock ring 674. The lock ring 674 includes a threaded end portion 678 for threaded engagement with a delivery member ring 680. The lock ring 674 holds the threaded section 678 to the delivery member during implantation of the helical anchor. FIG. 6B also shows the first end 651 of the tether extending from the first tether lumen 627 and the second end 652 of the tether extending from a hole in the driver knob 631.

To deploy the helical anchor of the system depicted in FIGS. 6A and 6B, anchor guide is inserted into the driver, the tether is inserted into the tether lumens of the system, and the driver is inserted into the delivery member. The driver is then advanced until the threaded section makes contact with the threads on the interior of the delivery member ring. At this point, the distal most tip of the anchor guide is just inside of the distal most portion of the delivery catheter. To advance the anchor guide from the delivery catheter, the threaded section is screwed into the delivery member ring. If the anchor guide is not made of a shape memory material that is set in a shape that corresponds to the shape of a portion of the valve annulus, the anchor guide is articulated into a curved shape as described above.

Screwing the threaded section into the delivery member ring to advance the anchor guide from the distal end of the delivery catheter also positions the distal end of the helical anchor so that it is just inside the distal tip of the delivery catheter. Once the anchor guide is extended, it is placed upon the valve annulus and the driver knob is turned to screw the threaded portion of the driver into the interior of the lock ring. When the bottom of the driver knob makes contact with the top of the lock ring, the helical anchor has been fully deployed from the delivery member. Once the helical anchor has been implanted, the delivery member and driver can be disengaged from the helical anchor by allowing the tether to slide freely in the tether lumens while withdrawing the delivery member, driver, and anchor guide in a proximal direction. If additional helical anchors are desired, the ends of the tether are threaded through an additional driver, helical anchor and delivery member based on where the preceding helical anchor was implanted and where the new helical anchor will be planted relative to the preceding helical anchor. It should be noted that because different embodiments of the current invention have different sized helical anchors, the lengths of various elements of different embodiments will vary based on the helical anchor size but the lengths of the delivery members will vary based on the delivery method and size of the patient.

Figure 7A:
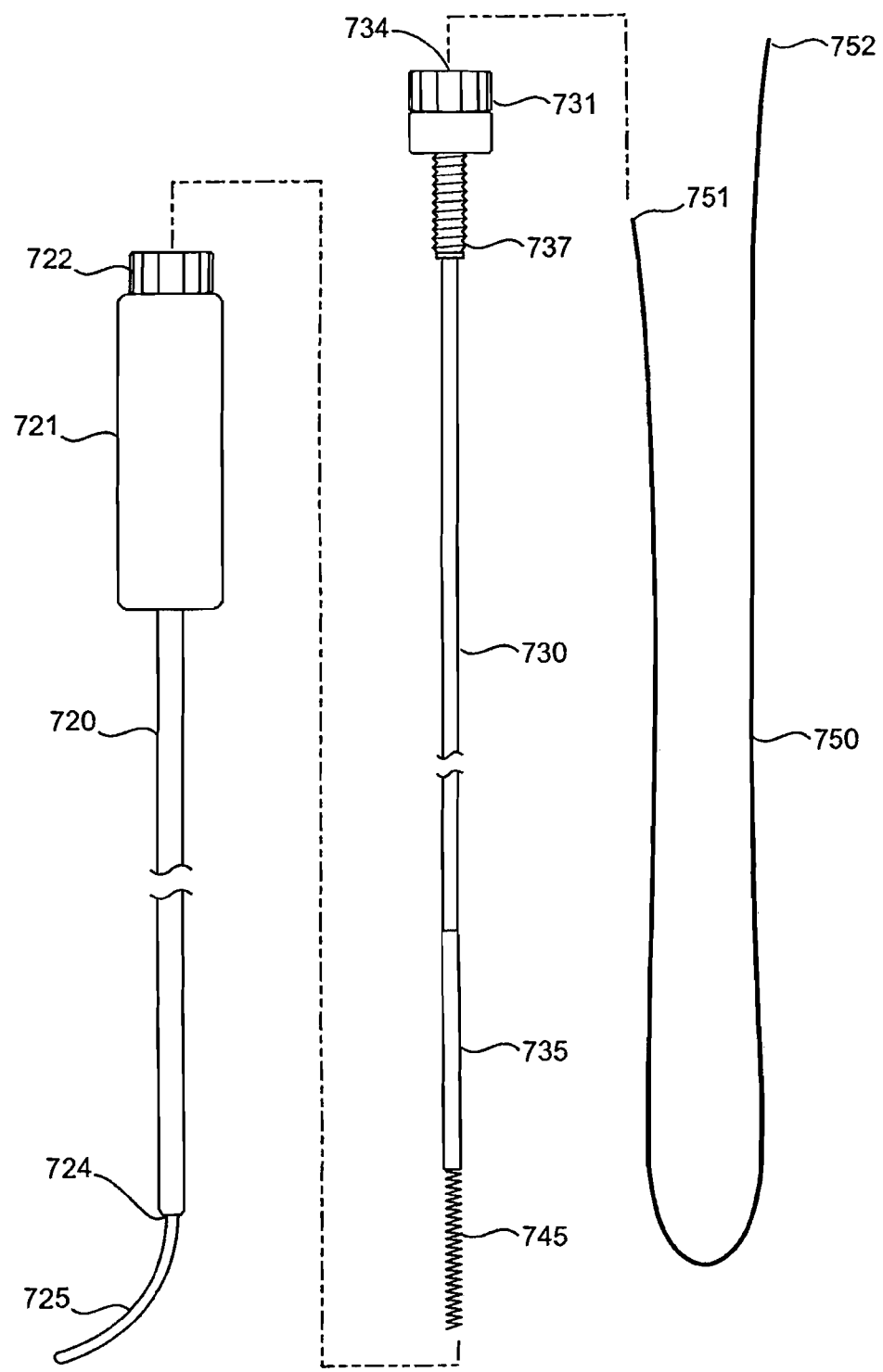
FIGS. 7A-7B illustrate an embodiment of an annulus modification system according to the current invention.
Figure 7B:
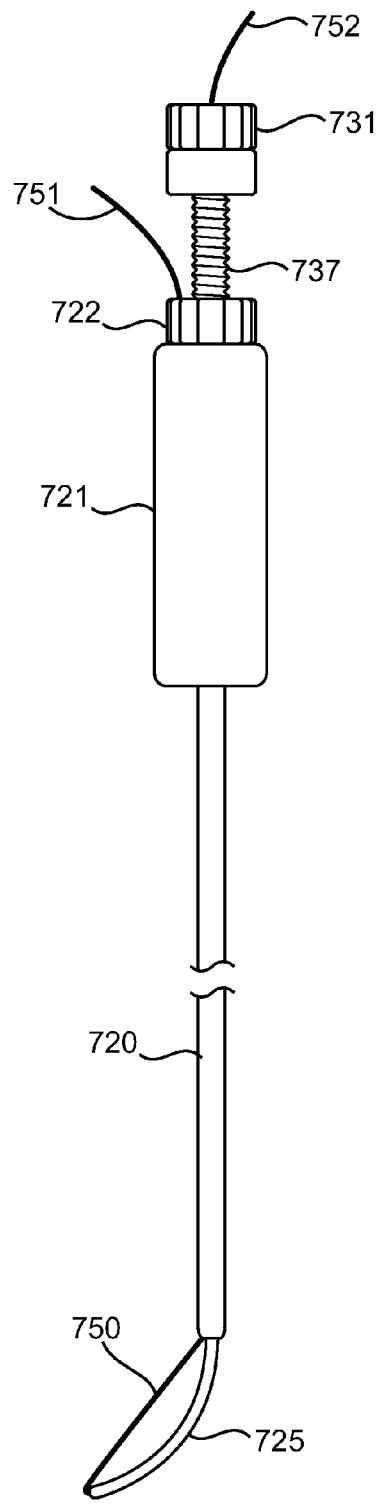
Figure 7C:
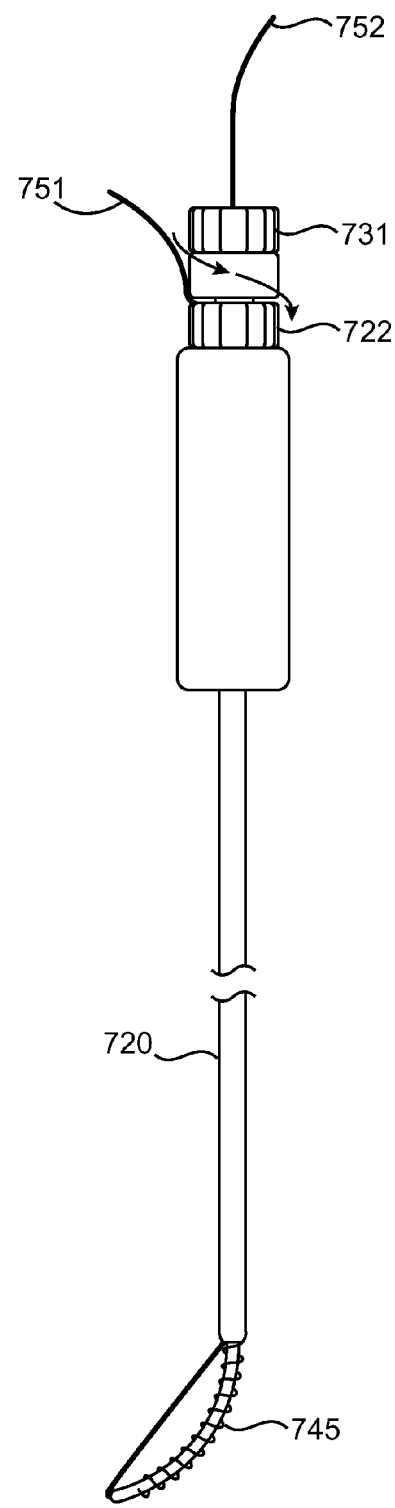

Referring now to FIGS. 7A-7C, there is shown an embodiment of a catheter based system used for a valve modification procedure where access is gained to a heart by navigating a catheter through a patient's vasculature. Using this procedure will allow a clinician to perform the procedure while the patent's heart is still beating. The system depicted in FIGS. 7A-7C has similar structure to the system depicted in FIGS. 3A-3C. The difference in the devices is that in the system of 7A-7C both the elongated delivery catheter and the elongated driver must be flexible so that they can be delivered to a heart valve through the vasculature, while the surgical based system of FIGS. 3A-3C does not require the flexibility that a catheter based system requires. The components of the system shown in FIGS. 7A-7C are made from the same biocompatible materials as the systems described above.

FIG. 7A shows the elongated generally tubular delivery member 720 having a handle 721 and a handle cap 722 on the proximal end of the delivery member 720. The distal end of the delivery member 720 includes an anchor guide 725 and the distal opening 724 of the driver lumen that communicates through the length of the delivery member.

The anchor guide 725 is configured to conform to the shape of at least a portion of the valve annulus when the anchor guide is placed next to a valve annulus at the treatment site. In one embodiment of the invention, the anchor guide is configured to conform to the annulus adjacent the posterior leaflet of a mitral valve. In another embodiment of the invention, the anchor guide is configured to conform to the annulus adjacent the anterior leaflet of a mitral valve.

An elongated helical anchor driver 730 includes a driver knob 731 on the proximal end of the driver and a threaded portion 737 adjacent the knob. A distal portion 735 of the driver is connected to a helical anchor 745. The driver can be made from any biocompatible material sufficient to allow the driver to rotate and to move longitudinally inside of the delivery member, and translate the rotation and movement to the helical anchor. The both the delivery member 720 and the driver 730 must be flexible enough to allow the system to negotiate the turns and curves required for an approach to a heart through a patient's vasculature.

Referring again to FIG. 7A, the system also includes a flexible elongated tether 750 having a first end 751 and a second end 752. The tether 750 is delivered to the treatment site in a looped configuration with first and second ends extending outside the patient's body during the implantation procedure. If additional helical anchors are desired, the ends of the tether are threaded through an additional driver, helical anchor and delivery member based on where the preceding helical anchor was implanted and where the new helical anchor will be planted relative to the preceding helical anchor.

To use the system, the first end 751 of the tether 750 is threaded into a tether lumen 734 at the proximal end of the driver and out through an inner channel of the helical anchor 745. The tether is then threaded into the driver lumen and into a tether lumen (not shown) in the anchor guide 725. The tether exits the end of the anchor guide and is routed back up through the driver lumen and exits the handle 721 through another tether lumen (not shown).

Referring to FIG. 7B, the driver having a driver knob 731 is inserted into the driver lumen of the delivery member 720 and advanced until the threaded portion 737 makes contact with a complementary threaded portion (not shown) on the interior of the delivery member handle 721 having a handle cap 722. When the driver has been advanced to the point where the threaded portion on the driver makes contact with the threaded portion on the handle, the helical anchor will be located adjacent to the anchor guide. The anchor guide 725 would then be aligned with a valve annulus and placed on the annulus in the desire location for implanting the helical anchor. Also shown in FIG. 7B is the tether 750 having a first end 751 and a second end 752.

Referring now to FIG. 7C, the driver knob 731 is rotated so that the threaded portion (not shown) on the driver is screwed into the complementary threaded portion (not shown) of the delivery member 720 having a delivery member cap 722. As the driver is threaded into the delivery member, the distal portion of the driver rotates and moves toward the distal opening of the delivery member until the distal end of the helical anchor 745 is extended from the delivery member and the distal end is rotated into and out of the valve annulus while the helical anchor is rotated along the anchor guide. Also shown in FIG. 7C is the tether having a first end 751 and a second end 752.

In some embodiments of the systems of the current invention, the helical anchor is engaged to the distal tip of the driver and the driver and helical anchor are placed in the delivery member such that the anchor guide is already in the inner channel of the helical anchor. In other embodiments, the extended distal tip of the helical anchor catches the anchor guide, as the distal end of the helical anchor extends from the distal opening of the delivery member, and the helical anchor rotates itself onto and along the delivery guide as the driver is threaded into the delivery member.

Once the helical anchor is implanted, the anchor guide is withdrawn into the delivery member. After the anchor guide is removed from the inner channel of the helical anchor, a portion of the tether remains disposed in the helical anchor such that one end of the tether extends from the distal end of the helical anchor and the other end of the tether extends from the proximal end of the helical anchor.

The delivery member and driver are then withdrawn from the area of the valve annulus. The tether slides freely through the tether lumens or other portions of the delivery member and driver while they are being withdrawn, and it can be completely removed from those portions of the system such that the ends extend outside of a patient's body while a portion of the tether is disposed in the inner channel of the helical anchor implanted in the patient's heart valve annulus.

In some embodiments of the invention where additional helical anchors are desired, the delivery member and driver are withdrawn and additional delivery members and drivers are selected. The tether is threaded into tether channels or other appropriate structure of the delivery members, drivers, and helical anchors such that the helical anchors can be implanted. The tether is threaded through the additional drivers, helical anchors, and delivery members based on where the preceding helical anchor was implanted and where the new helical anchor will be planted relative to the preceding helical anchor.

In at least one embodiment where multiple helical anchors are desired, the delivery member is left inside of a patient's body and the driver is withdrawn from the delivery member. The tether is threaded into an additional helical anchor and driver. The driver is then inserted into the delivery member and advanced so that the helical anchor is at the distal opening in the delivery member. The anchor guide is then manipulated so that it is placed on the portion of the valve annulus where the additional helical anchor is desired, and the helical anchor is implanted as described above. Other additional helical anchors can be implanted using the same delivery member, or the delivery member can be withdrawn and other additional helical anchors implanted using additional delivery members and drivers as described above.

Once a desired number of helical anchors have been implanted, the clinician forms a loop out of the tether and makes the loop smaller to apply a force to the helical anchors and modify the shape of the valve annulus. When the shape of the valve annulus has reached a desired level of modification, the tether is tied using a traditional surgeons knot so that the valve annulus will be maintained in the desired state of modification. Any excess material on the tether is then trimmed away.

Figure 8:
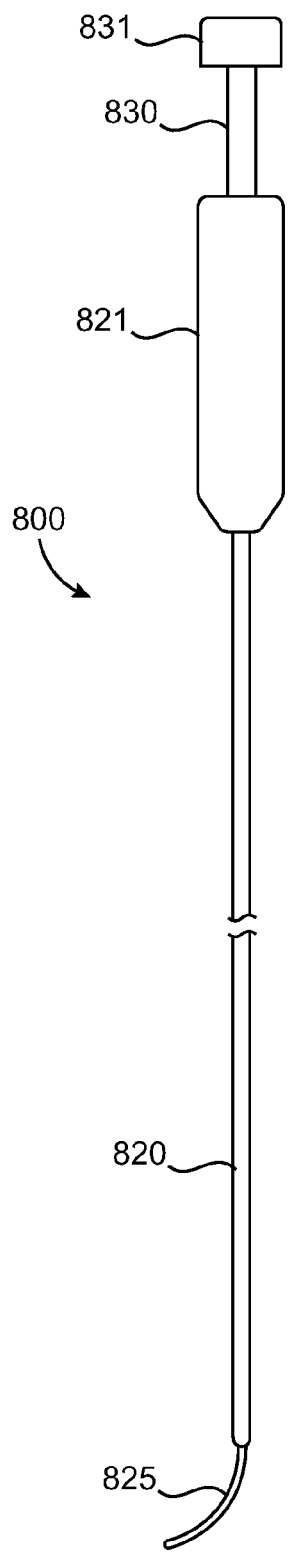
FIGS. 8 and 9 illustrate embodiments of delivery members that are used in annulus modification systems according to the current invention.
Figure 9:
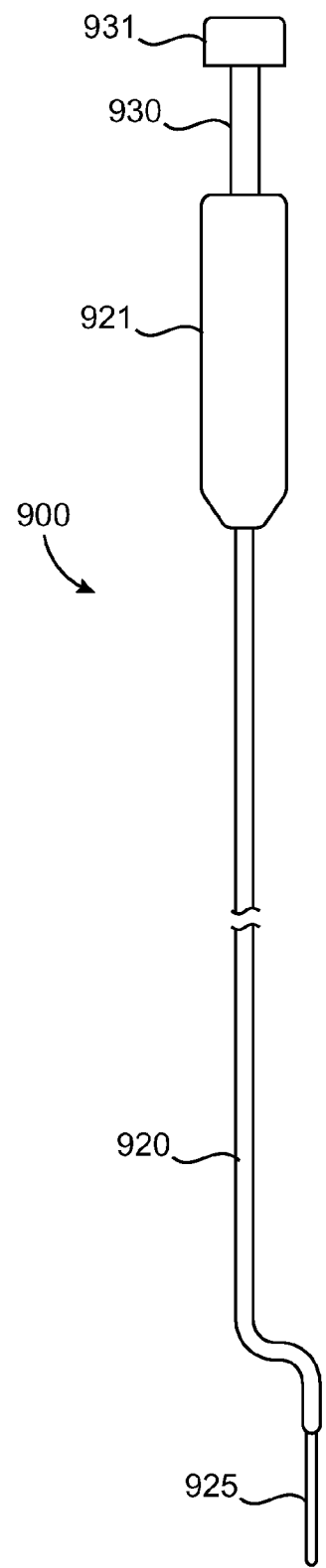

FIGS. 8 and 9 illustrate other embodiments of annulus modification systems in accordance with the present invention. The systems depicted in the figures can be used for implanting helical anchors using a minimally invasive surgical procedure. The systems include many of the same components as those systems described above and thus will not be described in great detail. Referring to FIG. 8, system 800 comprises a system having an elongated tubular helical anchor 820 with an anchor guide 825 on the distal end thereof. A handle 821 is located on the proximal end of the delivery member. A driver 830 is disposed in a helical anchor lumen (not shown). A driver knob 831 is disposed on the proximal end of the driver, and a helical anchor (not shown) is disposed on the distal end. A tether (not shown) is disposed within the driver and delivery member. The anchor guide has a curved shaped to correspond with the shape of a portion of the heart valve. The system includes other components similar to those described above and it works the same way as those described above.

Referring now to FIG. 9, system 900 comprises a system having an elongated tubular helical anchor 920 with an anchor guide 925 on the distal end thereof. A handle 921 is located on the proximal end of the delivery member. A driver 930 is disposed in a helical anchor lumen (not shown). A driver knob 931 is disposed on the proximal end of the driver, and a helical anchor (not shown) is disposed on the distal end. A tether (not shown) is disposed within the driver and delivery member. The anchor guide of the depicted embodiment has a relatively straight shape for use in implanting helical anchors along relatively straight portions of a valve annulus. The system includes other components similar to those described above and it works the same way as those described above.

Figure 10:
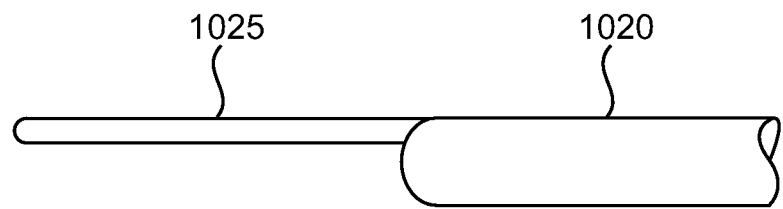
FIGS. 10-17 illustrate a variety of shapes for anchor guides in annulus modification systems according to the current invention.
Figure 11:
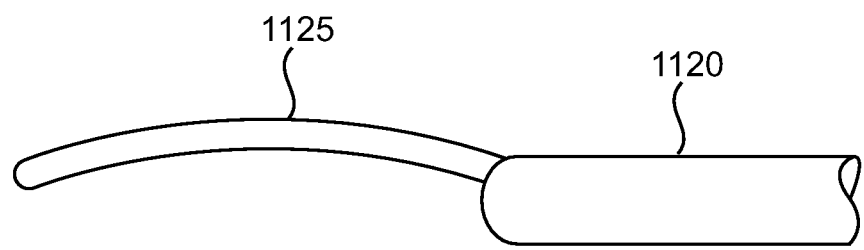
Figure 12:
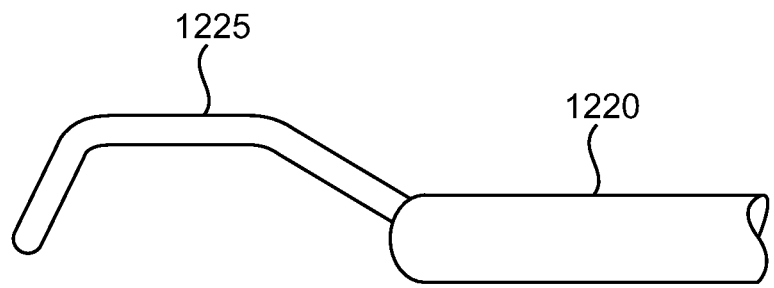
Figure 13:
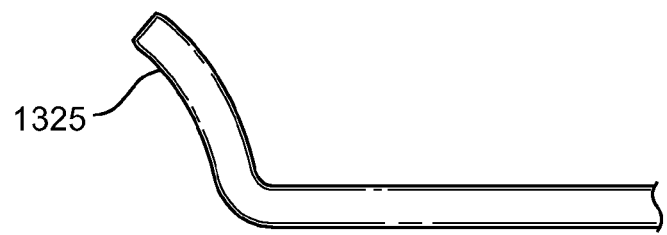
Figure 14:
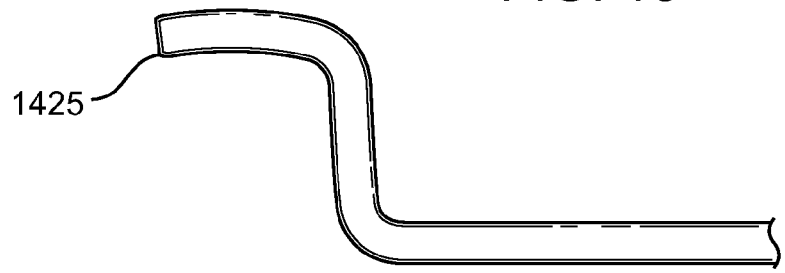
Figure 15:
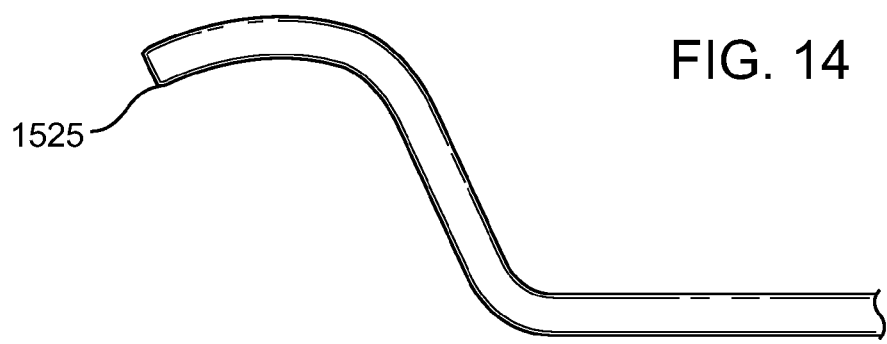
Figure 16:
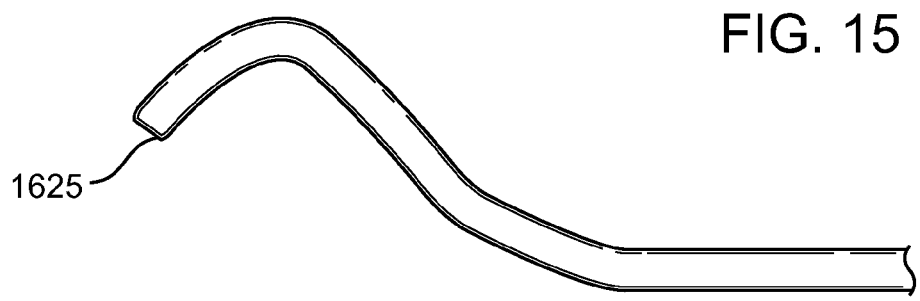
Figure 17:
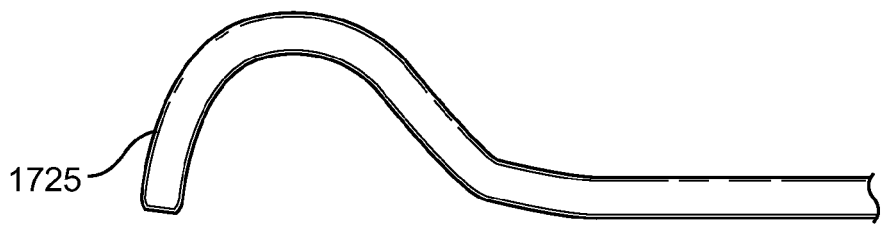

FIGS. 10 through 17 illustrate the variety of shapes that the anchor guides of the current invention can have. FIG. 10 shows the distal end of a delivery member 1020 having a generally linear anchor guide 1025. The linear anchor guide can be used for implanting helical anchors in a location where a valve annulus is relatively straight. FIG. 11 shows the distal end of a delivery member 1120 having a large radius curve anchor guide 1125 that is suited for implanting helical anchors where a valve annulus has a gentle/large radius curvature. FIG. 12 depicts the distal end of a delivery member 1220 having an anchor guide 1225 with a plurality of straight sections along its length. The anchor guide depicted in FIG. 12 is suited for a valve annulus that has a very tight curve radius at a location where a helical anchor is desired. In another embodiment (not depicted) the anchor guide can have a plurality of curved sections having different radii for implanting a helical anchor on a section of a valve annulus where the radius of curvature changes along the annulus. FIGS. 13 through 17 illustrate a plurality of anchor guides 1325 (FIG. 13), 1425 (FIG. 14), 1525 (FIG. 15), 1625 (FIGS. 16), and 1725 (FIG. 17) having a variety of shapes. A clinician can choose delivery members for implanting helical anchors based on the size of the valve annulus, the shape of the valve annulus, the shape of the delivery member relative to the shape valve annulus, and the length of the helical anchor to be implanted.

Various embodiments of the current invention include annuloplasty devices comprising a single helical anchor and a tether or a plurality of helical anchors and a tether. After the helical anchors of the various embodiments are implanted in a heart valve annulus, the tether is manipulated to apply a force to the helical anchors and modify the shape of the heart valve annulus. In some cases, the tether is formed into a loop and the loop is made progressively smaller until a desired degree of modification has been achieved at which time either a knot or other locking device is placed on the tether to secure the loop and maintain the desired state of annulus modification.

In other cases a bead or other device that is too big to pass through the inner channel of a helical anchor is secured to one end of the tether and tension is applied to the other end of the tether to pull the bead against one end of a helical anchor. The application of tension is continued until the shape of the valve annulus has reached a desired state of modification and the tether is secured using another locking device on the other end of the helical anchor or group of helical anchors.

When the annuloplasty devices of the current invention are implanted using the traditional surgical approach (as described above), the clinician can tie the ends of the tether using a surgeon's knot or other knot to maintain the desired state of annulus modification. Similarly, when a single helical anchor is used and the clinician decides to alter the shape of the valve annulus and secure the ends of the tether to the helical anchor; the clinician can simply tie the ends of the tether to the helical anchor. Thus, the tether locking devices described immediately below are used more often for devices installed using minimally invasive surgical techniques (described below) or catheter based delivery (described below). However, the locking devices below can be used for annuloplasty devices installed using a more traditional surgical approach.

Figure 18A:
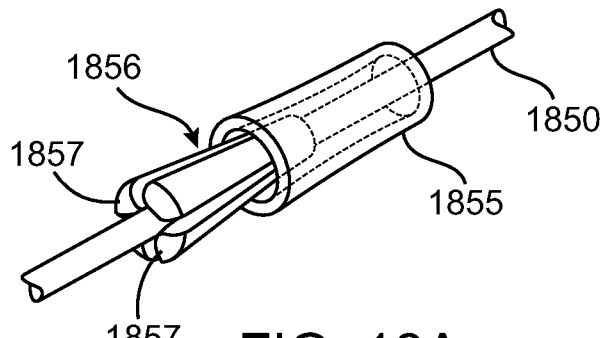
FIGS. 18A, 18B, and 19 illustrate embodiments of locking devices used for annuloplasty devices according to the current invention.
Figure 18B:
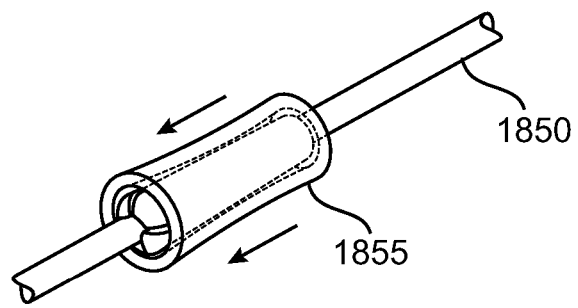

Referring now to FIGS. 18A and 18B, there can be seen a locking device according to the current invention. FIG. 18A shows the locking device having a stop member 1855 having a size and shape that will prevent the stop member from entering the inner channel of a helical anchor. In some embodiments of the invention, the stop 1855 will be smaller than the outer diameter of a helical anchor but larger than the diameter of the inner channel. This will allow the stop member to be delivered through a delivery member or guide catheter.

As seen in FIG. 18A, the stop member has at least one lumen communicating through the stop member. A plurality of locking members 1856 can be spaced along the portion of the tether 1850 that will be inside of the helical anchors. The locking members 1856 have a proximal end and a distal end with a plurality of integral legs 1857 that extend at an angle from the locking member. The locking members are made from material having suitable flexibility to allow the legs to compress radially inward when pulled or otherwise moved through the stop member proximal end first, and then recoil radially outward so that they will not pass distally through the stop member. FIG. 18B shows that as the stop member is pushed distally (in the direction of the arrows) along the tether 1850, it is pushed over the locking member. Once the stop member has passed the locking member, it cannot move proximally along the tether unless the legs of the locking member are compressed radially inward.

The locking members can be tapered such that the outer diameter of the member at its proximal end is smaller than the outer diameter of the member at more distal locations. The largest outer diameter of the locking members is small enough to allow the locking members to pass through the tether lumen in the systems described herein that used stop members to secure the tether.

Figure 19:
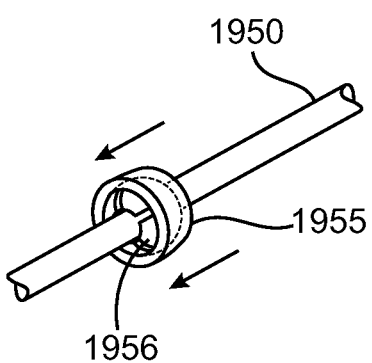

FIG. 19 shows another embodiment of a locking device having a shorter stop member 1955 and locking member 1956 on a tether 1950 than the stop member and locking member depicted in FIGS. 18A and 18B. In one embodiment of the invention, if a clinician determines that too much of the tension member has been withdrawn through the proximal helical anchor, a delivery sheath or similar device can be passed over the locking members to compress the legs inward. The sheath is then moved distally through the tether stop until the locking members are distal of the tether stop, at which time the sheath is withdrawn.

Other embodiments of stop members can have two biaxial lumens and the portion of the tether that is disposed in the inner channel of an annuloplasty device can have locking members at each end thereof, whereby the locking members at one end of the annuloplasty device are oriented in an opposite direction from the locking members at the other end of the annuloplasty device. In the embodiments having two lumens, the first and second ends of the tether are each passed through a different lumen and a force is applied to move the locking members through the lumens until the desired state of modification has been achieved.

In yet other embodiments having a single helical anchor, the tether can be secured to the helical anchor at one or both ends by stop members, and the tether can also be knotted to the stop members at one or both ends. Another method for securing the tether to a single helical anchor is to tie the tether to at least one end of the helical anchor.

Figure 20:
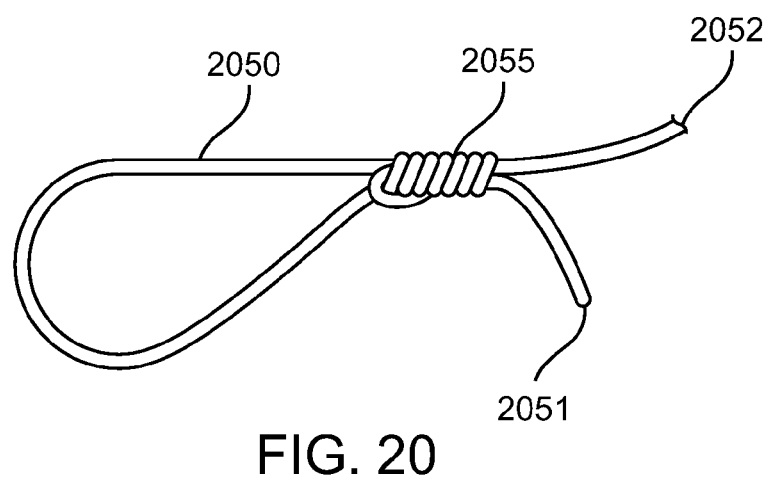
FIG. 20 illustrates an embodiment of a knot used as a locking devices used for annuloplasty devices according to the current invention.

In some embodiments of the invention the locking device is a knot or friction hitch that is tied such that it can move in one direction along the tether but not in another direction. One skilled in the art of knot tying will recognize that there are several such knots or hitches that would be suited for use as a locking device. Regardless of the knot/hitch used, the locking device must only be able to move distally along the tether, and it must not slip after a loop has been tightened to modify the shape of a valve annulus. Referring now to FIG. 20 there can be seen another locking device according to the current invention, wherein the locking device is a knot. The knot 2055 shown in the figure is a snell or snelled knot wherein one end 2051 of the tether 2050 is tied to the other end of the tether 2052 to form a loop. The knot 2055 is then moved distally along the other end 2052 of the tether toward a helical anchor to make the loop smaller until the desired state of modification in the valve annulus has been achieved.

The locking devices of the current invention can be made from any suitable biocompatible material including polymeric material such as, but not limited to, polyurethane, polyethylene, nylon and polytetrafluoroethylene (PTFE). The locking devices can be made from can be made from rigid plastics or metals such as stainless steel or other suitable metals, and it can be made from a combination of two or more of these materials. One embodiment of the current invention has tether stops and locking devices made from stainless steel and another embodiment has tether stops made from hard plastic and locking devices made from a shape memory alloy. Still another embodiment of the invention has tether stops made from stainless steel and locking members made from a flexible biocompatible polymer.

Regardless of the locking device used to secure the tether and maintain the desired level of modification of the valve annulus, the locking device will likely be placed on the tether at a location outside of a patient's body and then moved distally along the tether. Additionally, once the valve annulus has been modified and the locking device has been secured, any excess tether must be removed from the patient's body.

Figure 21A:
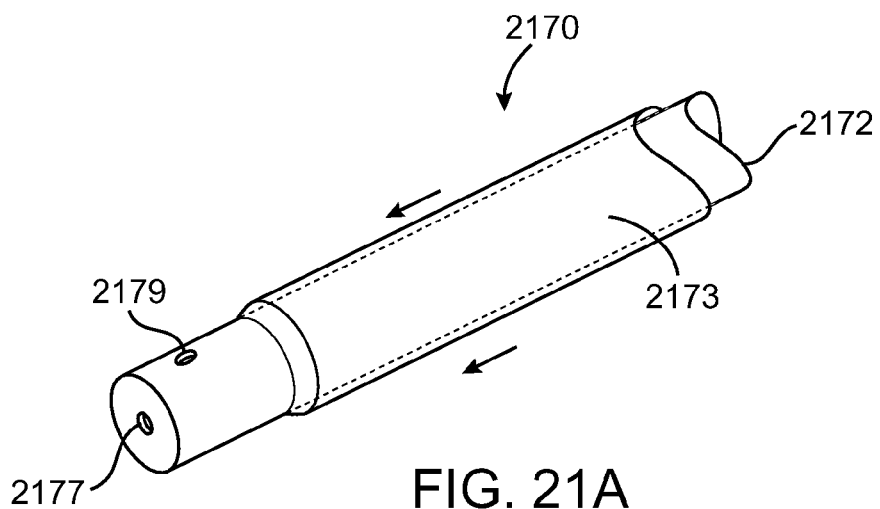
FIGS. 21A and 21B illustrates a lock pusher—tether cutter device according to the current invention.
Figure 21B:
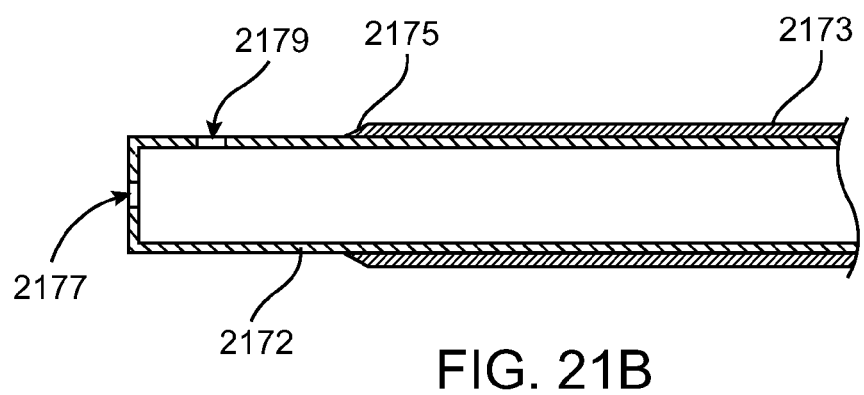

Referring now to FIG. 21A there is shown a lock pusher and tether cutting device 2170 according to the current invention. The lock pusher comprises a generally elongated tubular member 2172 disposed inside a cutting member 2173, the tubular member 2172 having a distal end, a proximal end, a tether channel, an exterior, and an opening 2177 in the distal tip of the elongated member. At least one tether portal 2179 communicates from the exterior of the lock pusher into the tether channel on the distal portion of the lock pusher. Referring specifically to FIG. 21B, the lock pusher is slidably disposed inside of a generally elongated cutting member 2173 that has a sharpened blade portion 2175 located at a distal end thereof, and a proximal end. The cutting member is disposed on the outside of the elongated tubular member 2172 with the opening 2177 in the distal tip of the elongated member and the at least one tether portal 2179 being distal to the blade portion.

Figure 22A:
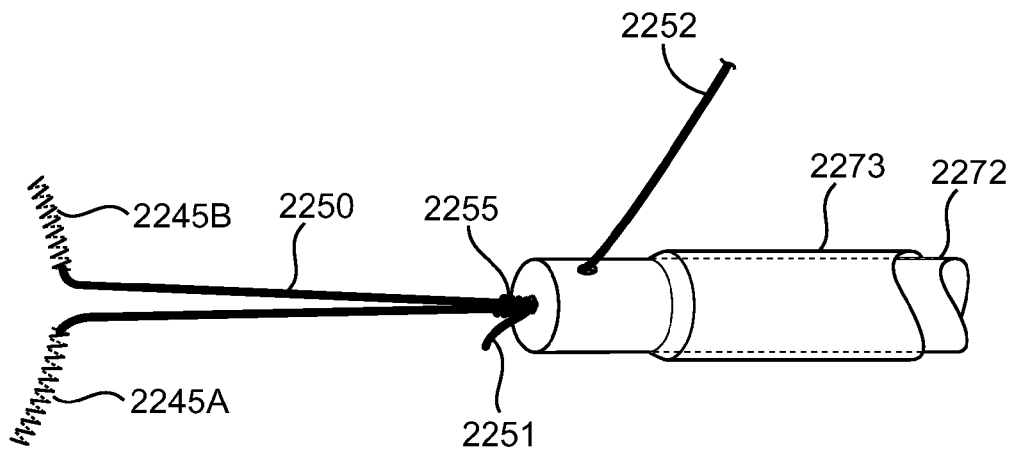
FIGS. 22A-22E illustrate a lock pusher—tether cutter device as it is used according to the current invention.

Referring to FIG. 22A, when the helical anchors 2245A and 2245B of an annuloplasty device according to the current invention is implanted in a heart valve annulus via minimally invasive surgery or delivered via catheter, the locking device 2255 will be placed on either the first end of the tether, the second end of the tether or both. The locking device is a knot 2255 made by tying the first end 2251 of the tether 2250 around a portion of the second end 2252 of the tether.

The locking device will then be moved for a short distance in a distal direction so that the free end or free ends of the tether can be inserted into the opening in the distal tip of the lock pusher tubular member 2272 and then extend out of a tether portal on the side of the tubular member and distal of the cutting member. The lock pusher will then be advanced to the helical anchor following the same path that the annuloplasty device delivery member followed. As the lock pusher is advanced distally from the ends of the tether a force is exerted on the helical anchor or helical anchors and the shape of the valve is modified.

Figure 22B:
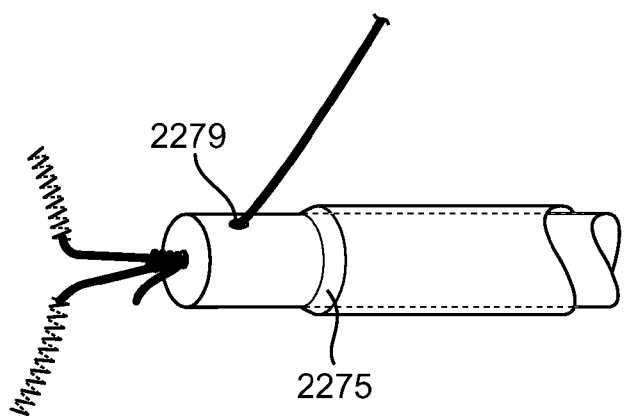
Figure 22C:
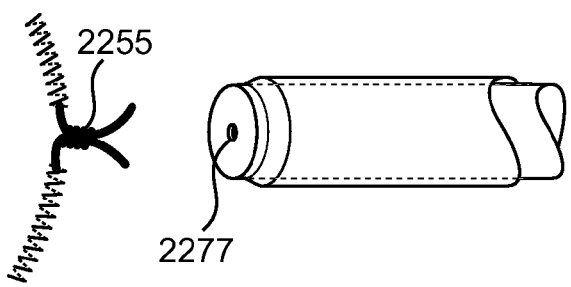

Referring now to FIG. 22B, once a desired level of modification is achieved, the clinician stops the distal movement of the lock pusher and secures the free ends of the tether to prevent them from moving distally. Once the free ends of the tether are secured, the cutting member is slid towards the helical anchors along the exterior of the lock pusher while the lock pusher is held in place. The sharpened blade portion 2275 on the distal end of the cutting member cuts the tether that is extending from the tether portal 2279 so that any excess tether can be removed from a patient's body. As can be seen in FIG. 22C, once the tether is cut, the lock pusher is then withdrawn from the patient's body such that the tether is removed from the opening 2277 in the distal tip of the lock pusher and the ends of the tether are secured by the knot 2255.

Figure 22D:
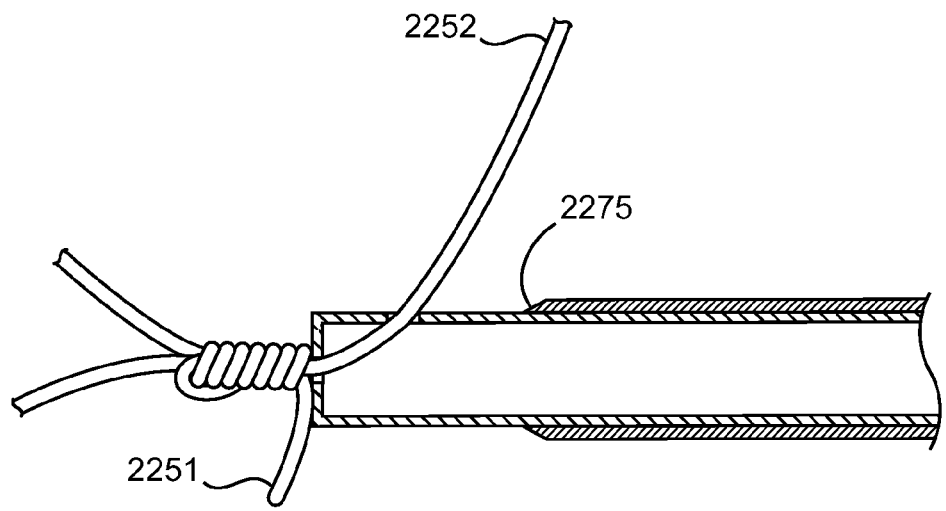
Figure 22E:
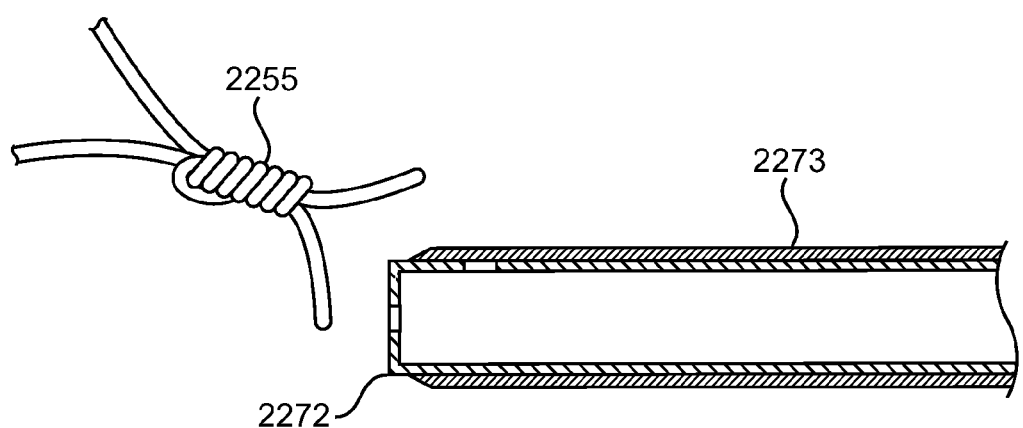

Referring now to FIG. 22D, the distance between the distal end of the lock pusher and the tether portal is sufficient to prevent a locking member that is just proximal of a tether stop, from exiting the tether portal and being cut from the tether. If a friction hitch or other knot is used or if one end of the tether is secured to a tether stop via a knot, only the first end 2251 of the tether will be free while the second end 2252 extends from the tether portal such that it can be cut by the sharpened blade portion 2275. As can be seen in FIG. 22E, once the cutting member 2273 is moved forward along the tubular member 2272 so that the sharpened blade portion cuts the tether that extends from the tether portal, the ends of the tether are secured by the knot 2255. Other embodiments of lock pushers according to the current invention can have the cutting member slidably disposed within the interior of the generally elongate tubular lock pusher.

If a tether stop having two biaxial lumens is used for a tether having locking members at both ends of the portion that is disposed within the inner channel of a helical anchor or helical anchors, one end of the tether is placed in the lock pusher while the other end is held outside of the patient's body. The lock pusher is then used to advance the tether stop distally to the helical anchor until the tether stop passes over one locking member. The lock pusher is then withdrawn and the other end of the tether is placed in the distal end of the lock pusher and out through the tether portal. The lock pusher is then advanced distally to engage the tether stop and advance the tether stop over the locking members on the tether until a desired degree of modification has been achieved for the valve annulus. The tether is then trimmed as described above and the lock pusher is withdrawn and used to trim the excess off of the other end of the tether as described above.

The components of the knot pusher and cutting member can be made from any suitable biocompatible material. The knot pusher can be made of flexible, biocompatible polymeric material such as, but not limited to, polyurethane, polyethylene, nylon and polytetrafluoroethylene (PTFE), it can be made from rigid plastics or metals such as stainless steel or other suitable metals, and it can be made from a combination of two or more of these materials.

The cutting member can also be made from flexible, biocompatible polymeric material such as, but not limited to, polyurethane, polyethylene, nylon and polytetrafluoroethylene (PTFE). Portions of the cutting member can be made from rigid plastics or metals such as stainless steel of other suitable metals as long as the distal portion of the driver is made from a flexible material that will allow it to negotiated curved portions of the delivery member. In one embodiment, the proximal portion of the cutting member is made from a flexible polymer and the sharpened blade portion is made from stainless steel and affixed to the distal end of the cutting member by a biocompatible adhesive.

The lumens of the lock pushers and cutting members of the current invention can be coated with a lubricious material such as silicone, polytetrafluroethylene (PTFE), or a hydrophilic coating. The lubricious interior surfaces facilitate the longitudinal movement the members relative to each other when the tether is being trimmed.

After the procedure is complete, the location of the locking device will be based on the number of helical anchors, the method used to deploy the helical anchors and the desire of the clinician. When the annuloplasty devices of the current invention are used to treat mitral regurgitation, it is possible to place the helical anchor device at any desire location along the valve annulus that does not have a helical anchor implanted in it. The most common locations for leaving the helical anchor when treating mitral regurgitation are along the annulus at a location adjacent the posterior commisure, at a location adjacent near the left trigone, at a point that is located along the anterior portion of the annulus, at a location near the right trigone, and at a location adjacent to the anterior commisure. Locking devices are generally located adjacent the posterior commisure or left trigone when the annuloplasty devices of the current invention have been implanted using a minimally invasive surgical procedure. Locking devices age generally located near the anterior commisure or right trigone when the annuloplasty devices are implanted using a catheter based method.

If the annuloplasty device uses a single helical anchor or if the clinician chooses to put a helical anchor stop or knot at each end of the device, as opposed to forming a loop, then the force is applied to reshape the annulus based on the method of access to the mitral valve. Access via a minimally invasive surgical procedure usually means that the shape modification force is applied from the proximal commisure or left trigone area. Access via a catheter based method usually means that the modification force is applied from the anterior commisure or right trigone area.

When a clinician is manipulating the tether of the current invention to modify the valve annulus of a beating heart, such as with a minimally invasive surgical procedure of a catheter based procedure, the degree of modification can be monitored using fluoroscopy or any other imaging procedure that is known for measuring valvular regurgitation. Once the desired degree of modification has been achieved, the tether is secured using a locking device as described above.

To achieve the desired degree of modification, a treating clinician must take care to not exert too much force on the valve annulus. Thus, the clinician should apply a force slowly and increase it incrementally while continuously monitoring. A clinician can also use a device for measuring the amount of force applied to ensure that not too much force is being used. This assists the clinician in making sure that the helical anchor is not pulled out of the valve annulus by too much force. In an embodiment having a single helical anchor implanted on the posterior portion of a mitral valve annulus between the posterior commisure and the anterior commisure and a single helical anchor along the anterior portion of the mitral valve annulus between the left and right trigone, maximum modification can be achieved by applying a constant tension force of six pounds close a loop and leave the helical anchor at a location adjacent to either the posterior commisure or the anterior commisure while constantly monitoring to check on the level of mitral regurgitation. In a single helical anchor embodiment or a multiple helical anchor embodiment implanted along the posterior commisure, and not using a loop, maximum modification can be achieved by applying constant tension force of just over four pounds from either end of the helical anchor or helical anchors. Once the desired state of modification has been achieved, and the tether lock has been placed, the annuloplasty device remains under a force load.

Figure 23:
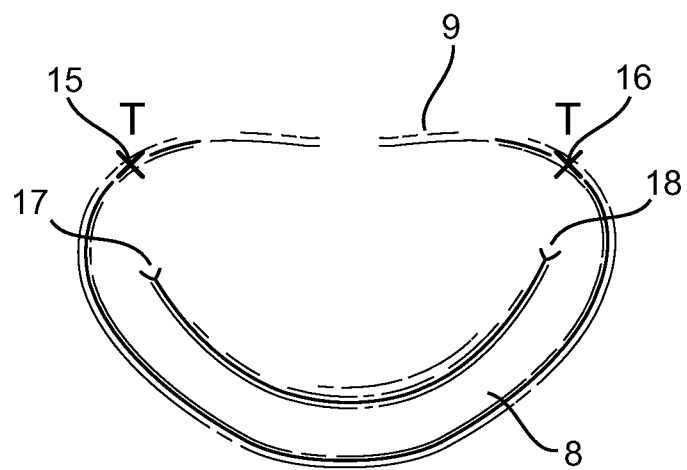
FIG. 23 illustrates the anatomy of a mitral valve.

FIG. 23 illustrates a mitral valve with the rest of the heart structure removed for clarity. The valve has a posterior commisure 17, an anterior commisure 18, an annulus with a posterior portion 8 and an anterior portion 9. A left trigone 15 and a right trigone 16 are located along the anterior portion of the annulus.

FIGS. 24 to 28 illustrate a variety of embodiments of annuloplasty devices according to the current invention. The devices shown in the FIGS. can be implanted in a temporarily stopped heart using a traditional surgical method for accessing the valve. The devices can also be implanted in a beating heart using a minimally invasive surgical methods or catheter based methods to access the valve. As can be seen in FIGS. 24-28, the devices are implanted such that the helical anchors are generally parallel to the plane created by the mitral valve annulus; or stated another way, the length or long axis of the anchors is generally parallel to the valve annulus. To provide for clarity in the illustrations, the tethers are not shown in the inner channels of the helical anchors of the FIGS.

Figure 24:
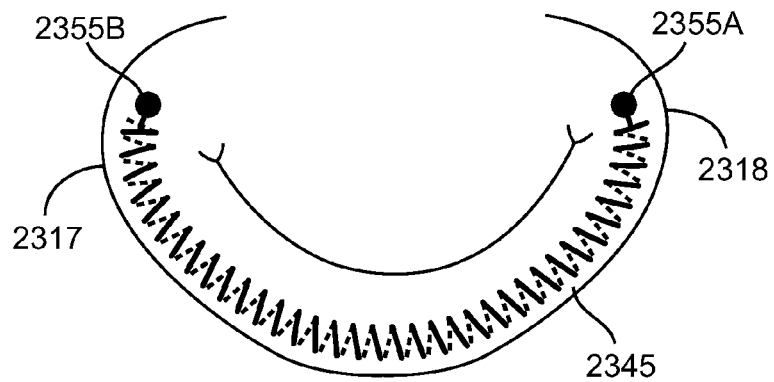
FIGS. 24-28 illustrate the placement of helical anchors and locking devices according to the current invention.

FIG. 24 illustrates a mitral valve having a single helical anchor 2345 implanted along the posterior portion of the annulus between the posterior commisure 2317 and the anterior commisure 2318. A tether (not shown) is disposed in the inner channel of the helical anchor and a pair of helical anchor stops 2355A and 2355B are disposed at the ends of the tether. The shape of the valve is modified by applying tension from either end of the helical anchor to shorten the length of the helical anchor along the annulus. In other embodiments of the invention having a single helical anchor, the tether can be tied to the helical anchor at one or both ends to secure the tether and to maintain the desired level of modification of the valve. Implanting a single helical anchor embodiment or a multiple helical anchor embodiment on the posterior side of a mitral valve annulus allows a clinician to avoid the portion of the valve near the aorta and thus reduces the potential for piercing the aorta wall.

Figure 25:
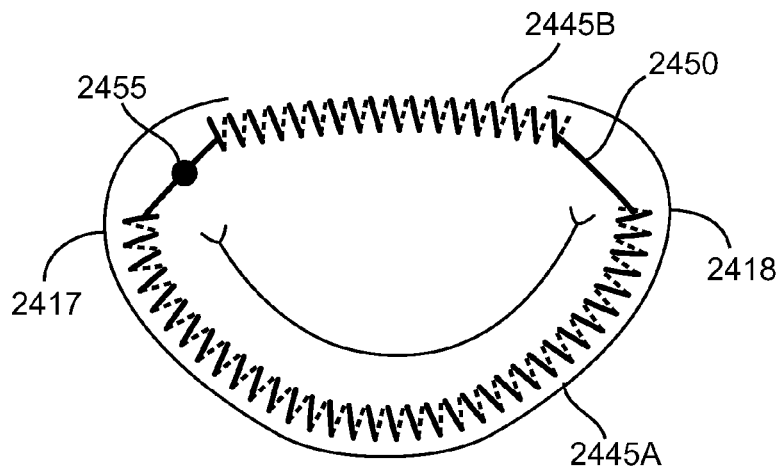

FIG. 25 illustrates an annuloplasty device according to the current invention having a single helical anchor 2445A implanted along the posterior portion of a mitral valve annulus between the posterior commisure 2417 and the anterior commisure 2418. Another helical anchor 2445B is implanted along the anterior portion of the valve annulus between the left and right trigones. A tether 2450 is disposed in the inner channels of the helical anchors and a tether lock 2455 is located at a point along the helical anchor that is adjacent to the posterior commisure. In this embodiment, the shape of the valve is modified by applying a force to make the loop in the tether smaller until the desired level of modification has been achieved and a locking device is placed on the tether to maintain the desired state of modification.

Figure 26:
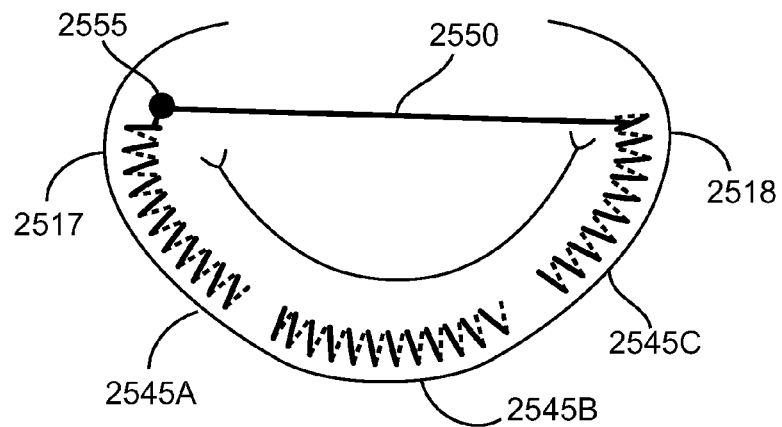

FIG. 26 illustrates a mitral valve having three helical anchors 2545A, 2545B, and 2545C implanted along the posterior portion of the annulus between the posterior commisure 2517 and the anterior commisure 2518. A tether 2550 is disposed in the inner channels of the helical anchors and a locking device 2555 is located adjacent to the posterior commisure. In this embodiment, the shape of the valve is modified by applying a force to make the loop in the tether smaller until the desired level of modification has been achieved and a locking device is placed on the tether to maintain the desired state of modification. In other embodiments having multiple helical anchors along the posterior portion of the annulus, a clinician may choose not to form a loop from the tether and the shape of the valve is modified by applying tension from either end of the group of helical anchors to shorten the length of the helical anchors along the annulus.

Figure 27:
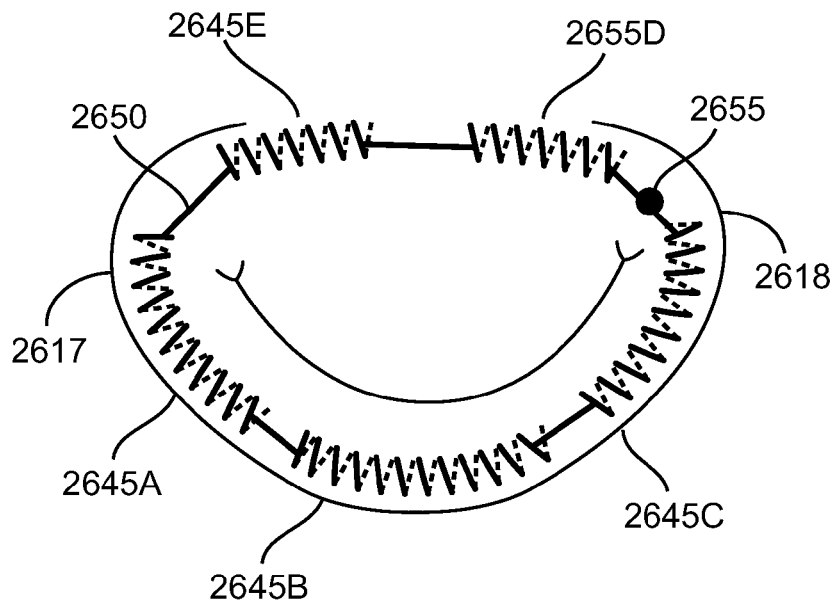

FIG. 27 illustrates a mitral valve having three helical anchors 2645A, 2645B, and 2645C implanted along the posterior portion of the annulus between the posterior commisure 2617 and the anterior commisure 2618, and a pair of helical anchors 2645D and 2645E along the anterior portion of the valve annulus between the left and right trigones. A tether 2650 is disposed in the inner channels of the helical anchors and a tether lock 2655 is located at a point along the helical anchor that is adjacent to the anterior commisure. In this embodiment, the shape of the valve is modified by applying a force to make the loop in the tether smaller until the desired level of modification has been achieved and a locking device is placed on the tether to maintain the desired state of modification.

Figure 28:
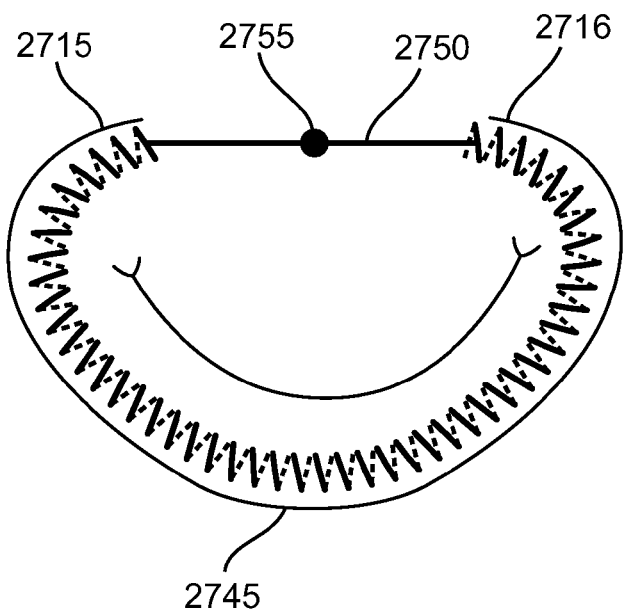

FIG. 28 illustrates a mitral valve having a single helical anchor 2745 implanted along the posterior portion of the annulus between left trigone 2715 and the right trigone 2716. A tether 2750 is disposed in the inner channel of the helical anchor and a locking device 2755 is located along the anterior portion of the annulus. In this embodiment, the shape of the valve is modified by applying a force to make the loop in the tether smaller until the desired level of modification has been achieved and a locking device is placed on the tether to maintain the desired state of modification. In other embodiments having a single helical anchor, a clinician may choose not to form a loop from the tether and the shape of the valve is modified by applying tension from either end of the helical anchor to shorten the length of the helical anchor along the annulus.

The helical anchors of the annuloplasty devices shown and discussed above are longitudinally implanted in an annulus of a heart valve. In embodiments using a single helical anchor, the number of coils per inch and the thickness of the material used for the helical anchors are selected to allow the helical anchors to be longitudinally contracted after they are implanted.

After the helical anchors are implanted in the annulus of a heart valve (as described above), a force is applied to the tether. The force on the tether modifies the shape of the valve annulus and increases coaption of the valve leaflets.

The helical anchors can be longitudinally implanted into a valve annulus via catheter based delivery or minimally invasive surgical delivery as described above. Additionally, all of the helical anchors of the current invention can be implanted during more traditional on bypass open heart surgical procedures.

One exemplary method that can be used for accessing a beating heart via minimally invasive surgical procedures to treat mitral regurgitation generally can start with intubating a patient with a double-lumen endobronchial tube that allows selective ventilation or deflation of the right and left lungs. The left lung is deflated, thereby helping to provide access to the surface of the heart. The patient is rotated approximately 30 degrees with the left side facing upwardly. The left arm is placed below and behind the patient so as not to interfere with tool manipulation during the procedure. While port positions depend to a large extent on heart size and position, in general a seventh and fifth space mid (to posterior) axillary port for tools and a third space anterior axillary port for the scope is preferable. A variety of endoscopes or thoracoscopes may be used including a 30-degree offset viewing scope or a straight ahead viewing scope. In general, short 10 to 12 mm ports are sufficient. Alternatively, a soft 20 mm port with an oval cross-section sometimes allows for two tools in the port without compromising patient morbidity.

Figure 29:
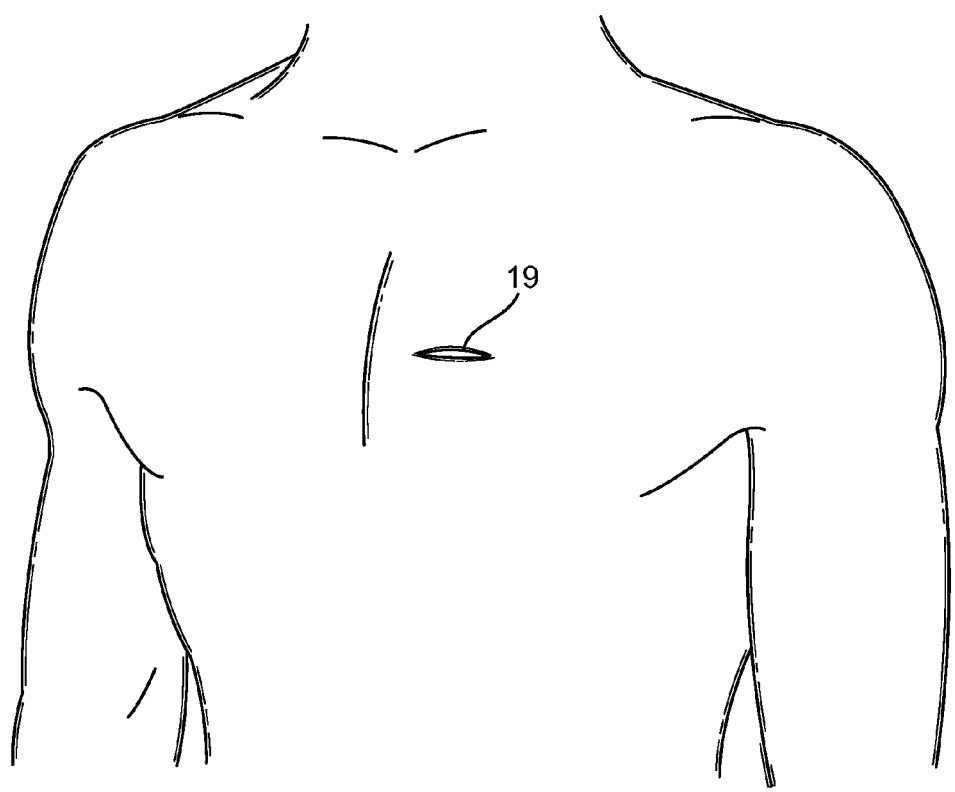
FIGS. 29-33 illustrate a minimally invasive surgical method for implanting helical anchored annuloplasty devices to treat mitral regurgitation according to the current invention.

In one embodiment of the present invention, passages are made through a patient's skin into the thoracic cavity, such as the passage 19 illustrated in FIG. 29. The passages may be formed by employing one-piece rods or trocars of prescribed diameters and lengths that are advanced through body tissue to form the passage, which are subsequently removed so that other instruments can be advanced through the passage. The passage may instead be formed by employing two-piece trocars that comprise a tubular outer sleeve, which is sometimes referred to as a port or cannula or as the tubular access sleeve itself, having a sleeve access lumen extending between lumen end openings at the sleeve proximal end and sleeve distal end. The two-piece trocar can further include an inner puncture core or rod that fits within the sleeve access lumen. The inner puncture rod typically has a tissue penetrating distal end that extends distally from the sleeve distal end when the inner puncture rod is fitted into the sleeve access lumen for use. The two-piece trocar can be assembled and advanced as a unit through body tissue, and then the inner puncture rod is removed, thereby leaving the tubular access sleeve in place to maintain a fixed diameter passage through the tissue for use by other instruments.

In one embodiment, a tubular access sleeve is placed through a passage that is made as described above in the chest wall of a patient between the patient's second rib and sixth rib, for example. The selection of the exact location of the passage is dependent upon a patient's particular anatomy. A further conventional tubular access sleeve can be placed in a different passage that is also made in the chest wall of patient.

In accordance with one method used in the invention, the patient's left lung is deflated to allow unobstructed observation of the pericardium employing a thoracoscope or other imaging device that is inserted through a sleeve lumen of a tubular access sleeve. The thoracoscope or other imaging device may have its own light source for illuminating the surgical field. Deflation of the patient's lung may be accomplished in a number of ways, such as by inserting a double lumen endotracheal tube into the trachea, and independently ventilating the right, left or both lungs. The left lung can be collapsed for visualization of the structures of the left hemisternum when ventilation of the left lung is halted and the left thoracic negative pressure is relieved through a lumen of the tubular access sleeve or a further access sleeve to atmospheric pressure. After deflation, the thoracic cavity may be suffused with a gas (e.g., carbon dioxide) that is introduced through a lumen of the tubular access sleeve or the further access sleeve to pressurize the cavity to keep it open and sterile. The pressurized gas keeps the deflated lung away from the left heart so that the left heart can be viewed and accessed and provides a working space for the manipulation of the tools of the present invention. It will be understood that the access sleeve lumens must be sealed with seals about instruments introduced through the lumens if pressurization is to be maintained.

A thoracoscope can then be inserted into the lumen of a tubular access sleeve to permit wide angle observation of the thoracic cavity by a surgeon directly through an eyepiece or indirectly through incorporation of a miniaturized image capture device (e.g., a digital camera) at the distal end of the thoracoscope or optically coupled to the eyepiece that is in turn coupled to an external video monitor. The thoracoscope may also incorporate a light source for illuminating the cavity with visible light so that the epicardial surface can be visualized. The thoracoscope may be used to directly visualize the thoracic cavity and obtain a left lateral view of the pericardial sac or pericardium over the heart.

The elongated access sleeve provides an access sleeve lumen, enabling introduction of the distal end of a pericardial access tool. The tubular access sleeve and the pericardial access tool are employed to create an incision in the pericardial sac so that the clinician can view and access the left free wall of the heart. After the clinician gains access to the heart, a continuous circular suture (commonly know and referred to herein as a purse string suture) is placed in the free wall of the left atrium at a location near the commisure of the mitral valve, and above the coronary sinus. The wall is then punctured inside the perimeter of the suture. The wall can be punctured using a special puncture device, or the distal end of the delivery members described herein can be used to puncture the wall.

The distal end of a first delivery member can then be advanced through the elongated access sleeve, through the puncture formed through the myocardium, and placed against the mitral valve annulus on either the anterior leaflet side (anterior side) or posterior leaflet side (posterior side) of the valve. At least a portion of a device for treating mitral regurgitation can then be implanted. The first delivery member is then withdrawn. The distal end of a second delivery member, which may be generally the same or different from the delivery member 10, is then advanced through the elongated access sleeve, through the puncture formed through the myocardium, and placed against the mitral valve annulus on the other of the anterior or posterior side of the valve. The remainder of the device for treating mitral regurgitation can then be implanted. The second delivery member is then withdrawn and the purse string is tightened to close the puncture. The lung can then be inflated, the instruments withdrawn from the patient, and all openings closed. The procedure outside of the heart can be viewed through a scope as disclosed above, and the procedure inside the heart can be visualized and imaged using fluoroscopy, echocardiography, ultrasound, EM imaging, other suitable means of visualization/imaging, or combinations of the aforementioned visualization methods. Visualization techniques may also be used to map the heart prior to beginning the minimally invasive procedure. Mapping the heart provides details as to the size and shape of the valve annulus to be treated and the extent of deformation of the valve, itself.

Figure 30:
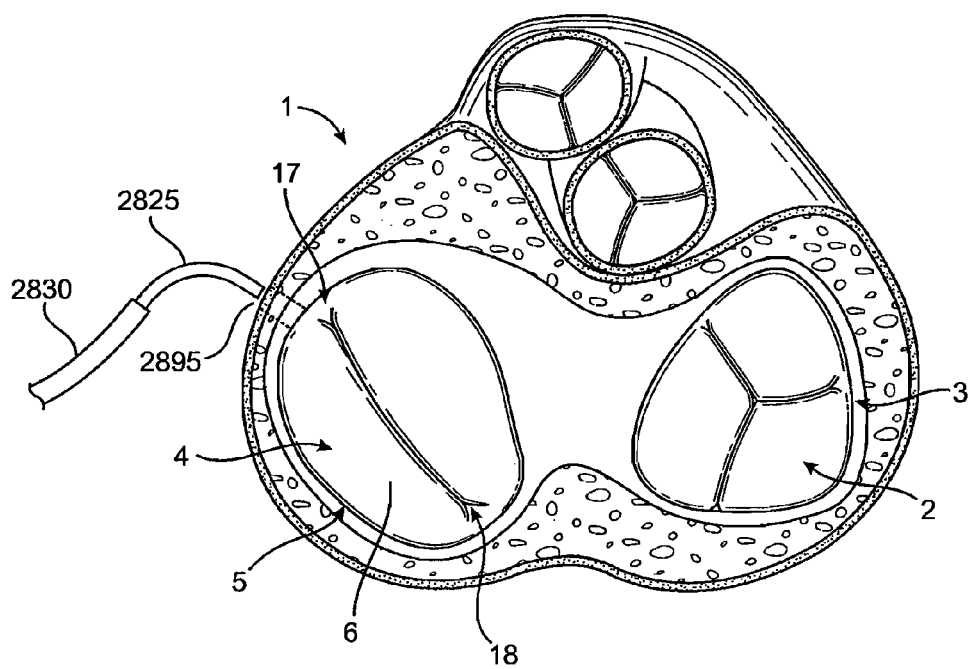
Figure 31:
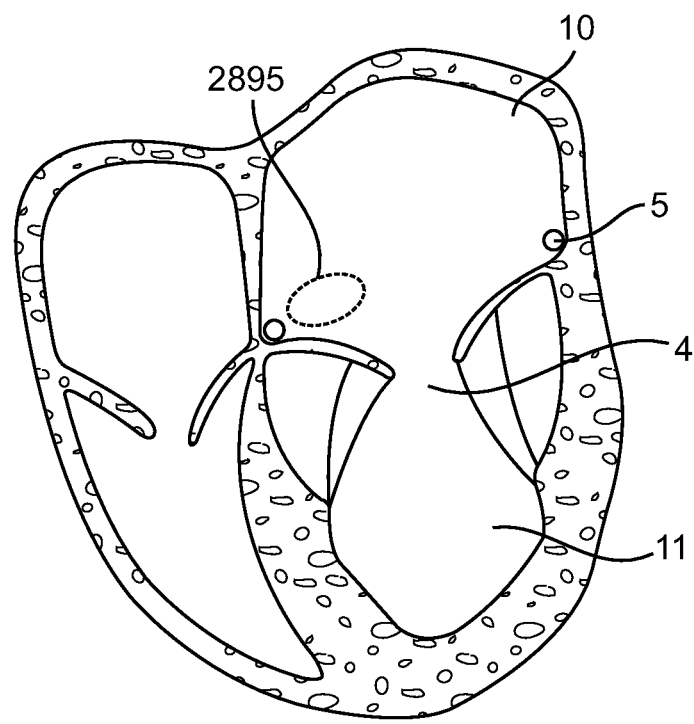
Figure 32:
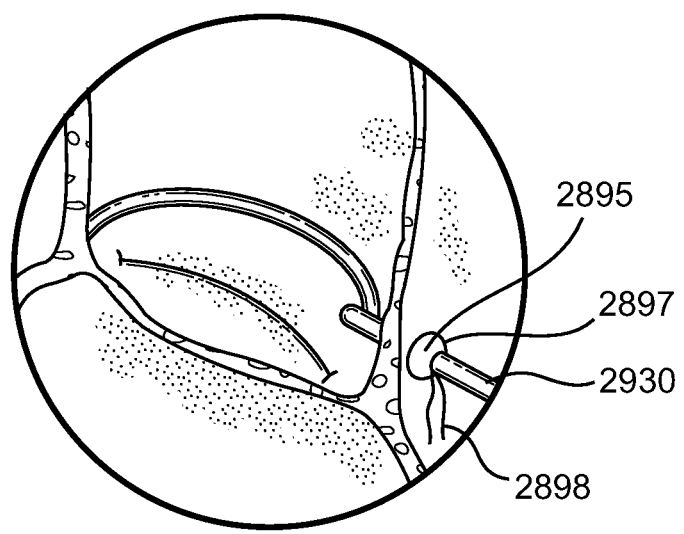

FIGS. 30, 31, and 32 illustrate an exemplary placement of delivery members of the current invention inside the heart. FIGS. 30 and 31 are illustrations showing cross-sectional views of a heart. FIG. 30 shows a heart 1 having tricuspid valve 2 and tricuspid valve annulus 3. Mitral valve 4 is adjacent mitral valve annulus 5. Mitral valve 4 is a bicuspid valve having anterior cusp and posterior cusp 6. Anterior cusp and posterior cusp 6 are often referred to, respectively, as the anterior and posterior leaflets. Also shown in the figure are the posterior commisure 17 and the anterior commisure 18. A purse string suture has been placed in the heart and the wall is punctured (as described above) at a location 2895 in the atrium wall that is adjacent the posterior commisure of the posterior and anterior cusp and above the coronary sinus. An elongated, generally tubular annuloplasty device delivery member 2830 having an anchor guide 2825 can then be placed into the heart and positioned on the valve annulus for implantation of an annuloplasty device having a single helical anchor or a plurality of helical anchors. FIG. 31 shows the puncture location 2895 in the wall of the left atrium 10, relative to the left ventricle 11, the mitral valve 4 and the mitral valve annulus 5.

Referring particularly to FIG. 32, the location of the puncture site 2895 is visible inside of the purse string suture 2897 (the free ends 2898 of the which are visible in the figure), and a portion of a delivery member 2930 is illustrated for delivering an annuloplasty device the posterior portion of a mitral valve annulus. A helical anchor can thereby be implanted in the correct location.

Figure 33:
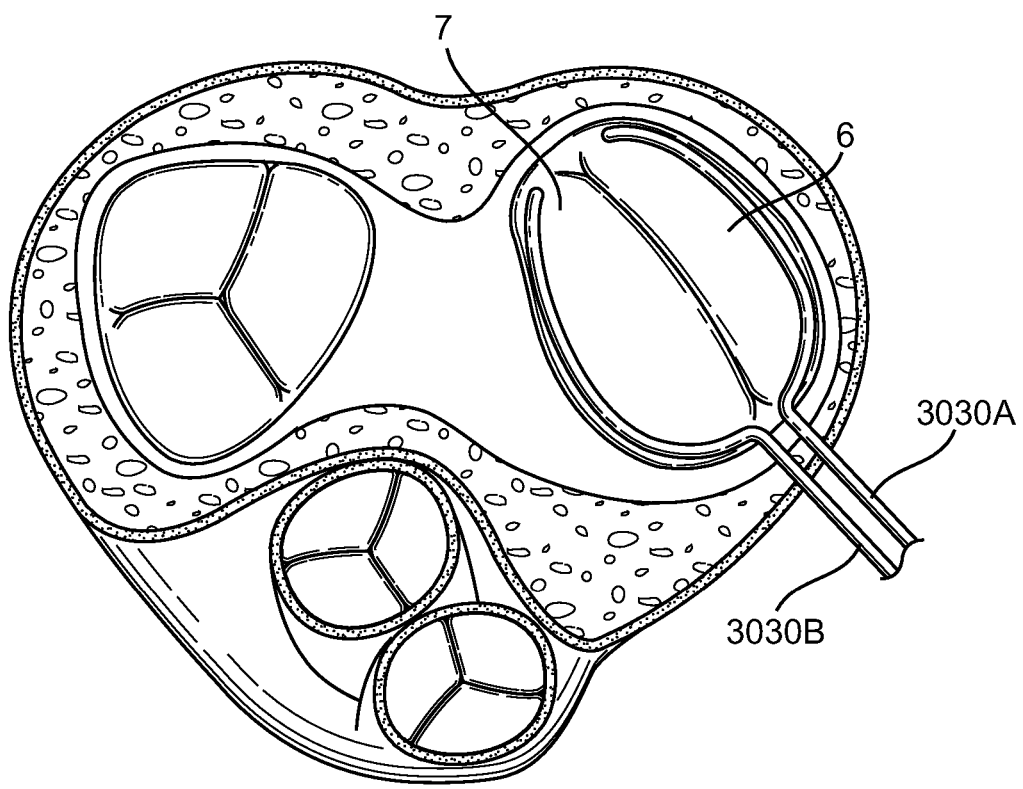

Referring now to FIG. 33, a schematic cross-section is illustrated showing two delivery members 3030A and 3030B on a mitral valve annulus. In practice, the delivery members are not inside of the heart at the same time, the figure shows how the posterior delivery member 3030A and the anterior delivery member 3030B are shaped to provide for insertion of helical anchors along a major portion of a valve annulus adjacent to the posterior cusp 6 and anterior cusp 7 of the mitral valve. The distal portions of the delivery members can be sized and shaped for a particular annulus based on the previously performed imaging and mapping. As is represented by the exemplary pronounced curvature of the distal section of the posterior delivery member in this figure, the distal section is relatively rigid so that the heart walls can be shaped to conform to the shape of the valve annulus and the device distal section for implantation of the helical anchor of a helically helical anchored device or ring.

Figure 34:
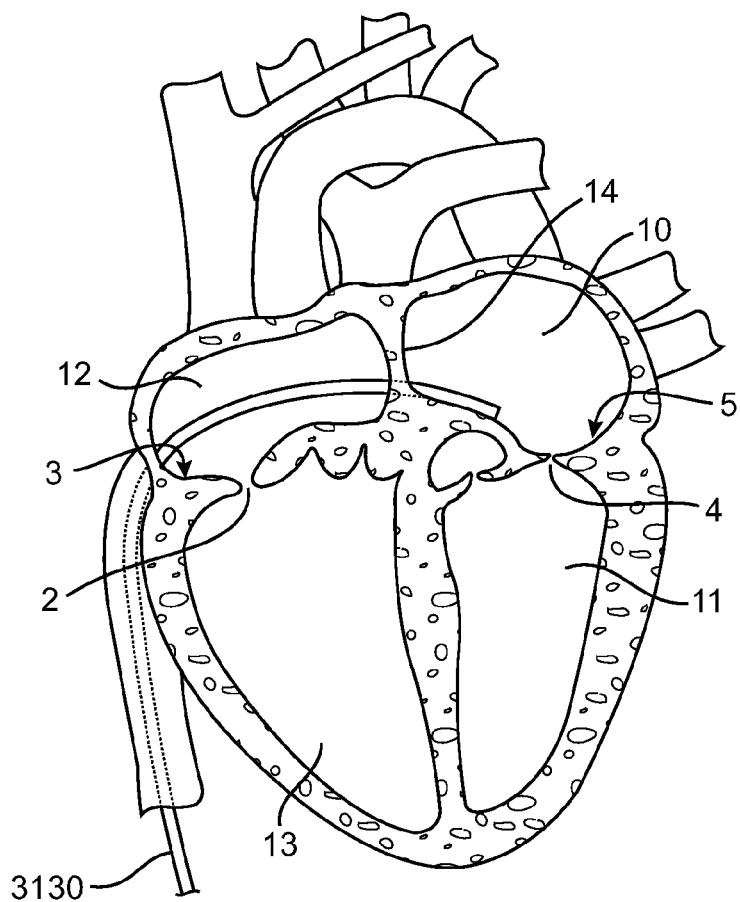
FIGS. 34 and 35 illustrate a catheter based method for implanting helical anchored annuloplasty devices to treat mitral regurgitation according to the current invention.
Figure 35:
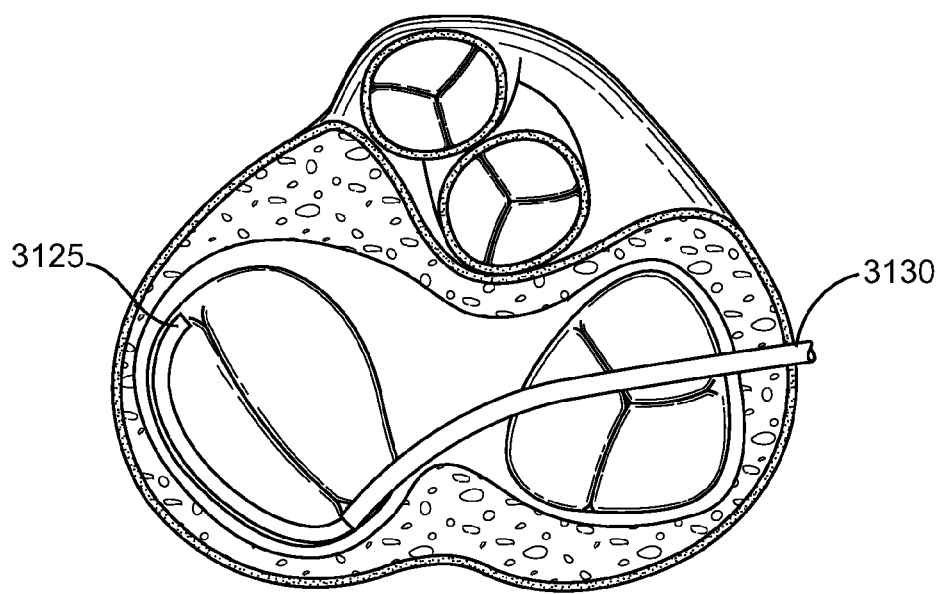

FIGS. 34 and 35 illustrate a catheter based method for implanting an annuloplasty device having a single helical anchor or a plurality of helical anchors. FIG. 34 is a longitudinal cross-sectional view of heart having left atrium 10, left ventricle 11, right atrium 12, right ventricle 13, mitral valve 4, mitral valve annulus 5, tricuspid valve 2 and tricuspid valve annulus 3. An elongated delivery catheter 3130 having an annuloplasty device with helical anchors according to the current invention is shown with the distal end of the delivery catheter in the in the left atrium. When using a catheter based method for implanting a helically helical anchored annuloplasty device, an elongate element (not shown), such as a guide catheter, having a lumen is first installed to provide a path for the annuloplasty device delivery catheter 3130 from the exterior of the patient to the left atrium. The annuloplasty device delivery catheter 3130 can then be advanced through the lumen so that the annuloplasty device can be implanted in a mitral valve annulus.

The device used for modifying the shape of the annulus is delivered using a catheter via the transeptal approach through the vena cava. The elongate element is inserted through the femoral vein into the common iliac vein, through the inferior vena cava into the right atrium 12. The transeptal wall 14 between the right atrium 12 and left atrium 10 is then punctured (preferably at the fossa ovalis) with a guide wire or other puncturing device. In one embodiment of the invention, a Brockenbrough® needle system as is currently known in the art can be used to puncture the septum.

Referring to FIG. 35; regardless of the method used to puncture the septum, the distal end of the catheter 3130 is advanced into the left atrium and the anchor guide 3125 is positioned adjacent the mitral valve annulus. The annuloplasty device can then be advanced through the lumen of the elongate element to the mitral valve for implantation into the mitral valve annulus. The anchor guide and helical anchor are advanced and rotated into the annulus in the manner discussed above in the description of FIGS. 6A and 6B.

Those skilled in the art will appreciate that alternative paths to gain access to the left atrium are available. For example, another possible path would be through the radial vein into the brachial vein, through the subclavian vein, through the superior vena cava into the right atrium, and then transeptally into the left atrium. Yet another possible path would be through the femoral artery into the aorta, through the aortic valve into the left ventricle, and then retrograde through the mitral valve into the left atrium.

Figure 36:
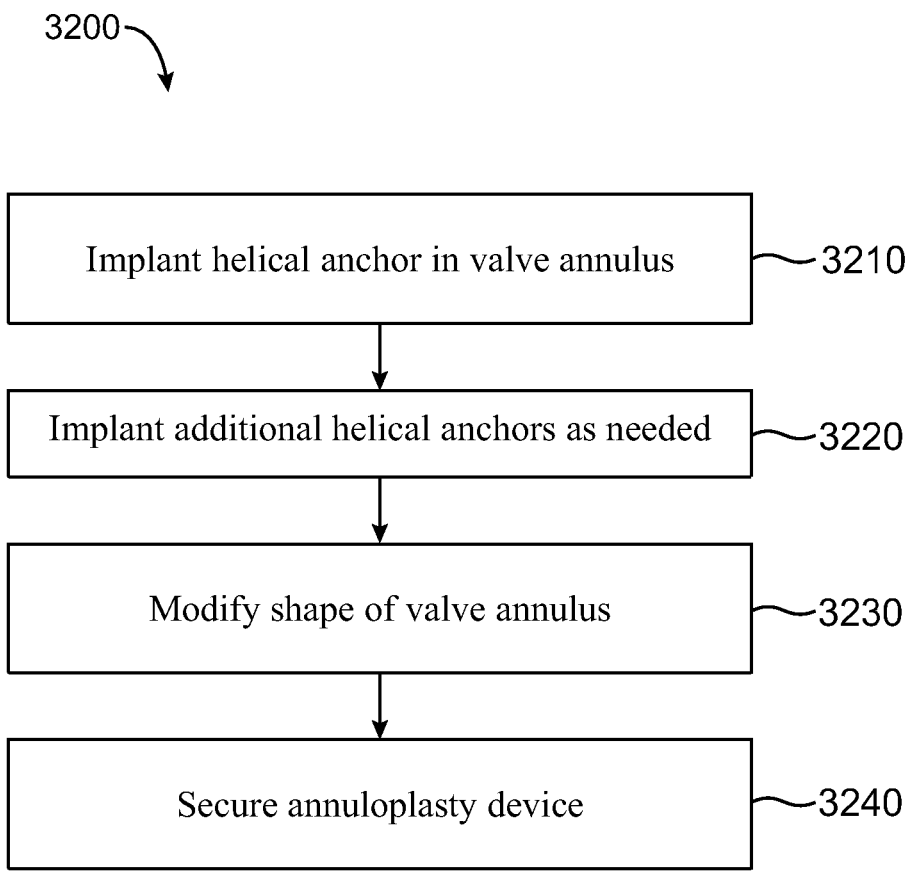
FIG. 36 is a flow chart showing one embodiment of a method for implanting a helically helical anchored annuloplasty device according to the current invention.

FIG. 36 is a flowchart illustrating one embodiment of a method 3200 to modify the shape of valve annulus according to the current invention. To practice the current invention a clinician accesses a heart valve and implants a helical anchor in the valve annulus 3210. Additional anchors can be implanted 3220 and the tether is manipulated to apply a force to the anchors and modify the shape of the valve annulus 3230. Once a desire degree of modification has been achieved, a locking device is placed on the tether to secure the annuloplasty device 3240 such that a desired level of modification has been achieved.

Figure 37:
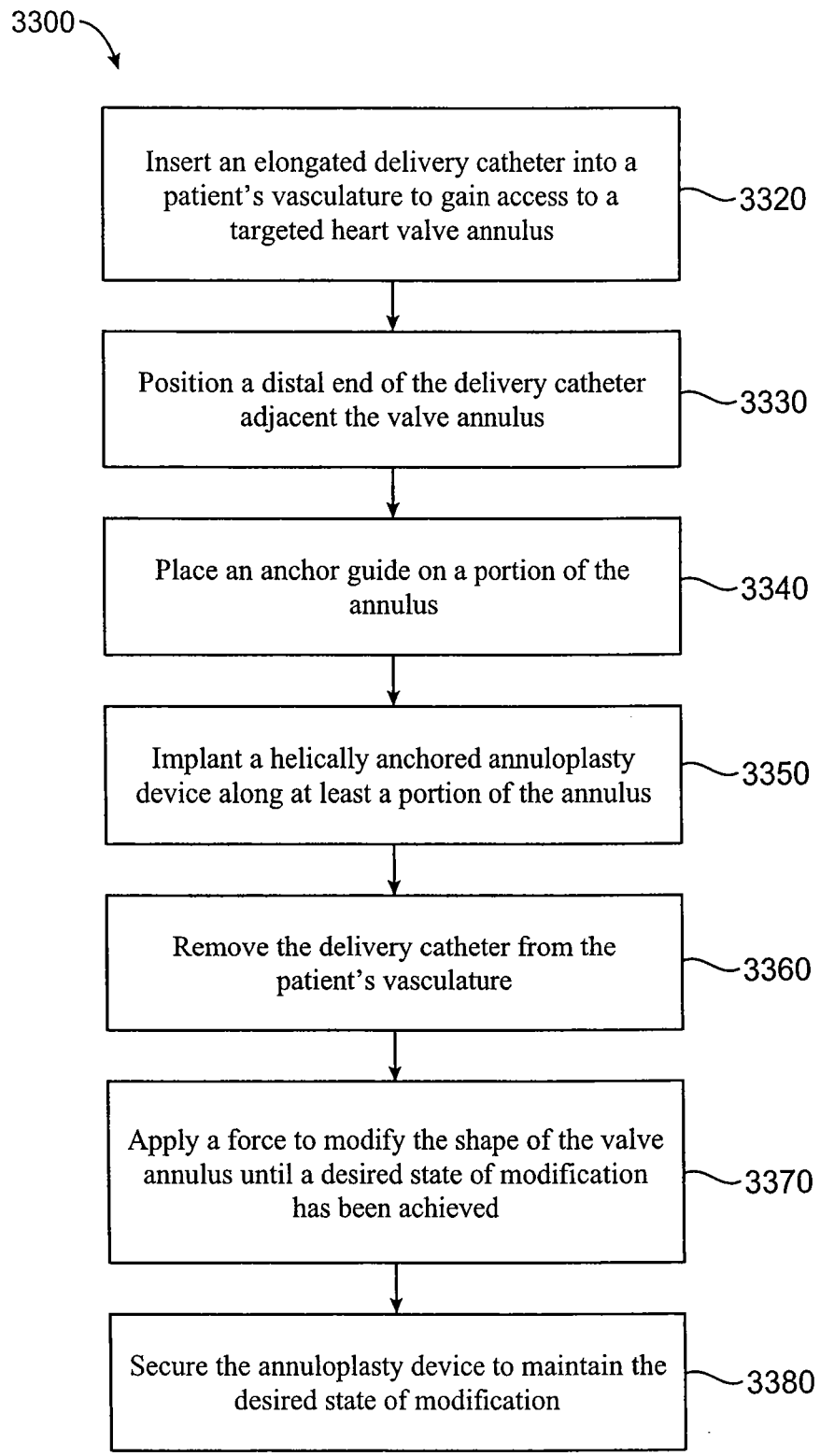
FIG. 37 is a flow chart showing one embodiment of a catheter based method for implanting a helically helical anchored annuloplasty device according to the current invention.

FIG. 37 is a flowchart illustrating one embodiment of a catheter based method 3300 to modify the shape of valve annulus according to the current invention. To begin the method, an elongated delivery catheter is inserted into a patient's vasculature to gain access to a targeted heart valve annulus 3320. The distal end of the catheter is positioned adjacent the valve annulus 3330, and the anchor guide is placed on a portion of the annulus 3340. A helically anchored annuloplasty device is then implanted along at least a portion of the annulus 3350. The delivery catheter is removed from the patient's vasculature 3360, and a force is applied to modify the shape of the valve annulus until a desired state of modification has been achieved 3370. Once a desired state of modification is achieved, a locking device is then used to secure the annuloplasty device and maintain the desired state of modification 3380.

Figure 38:
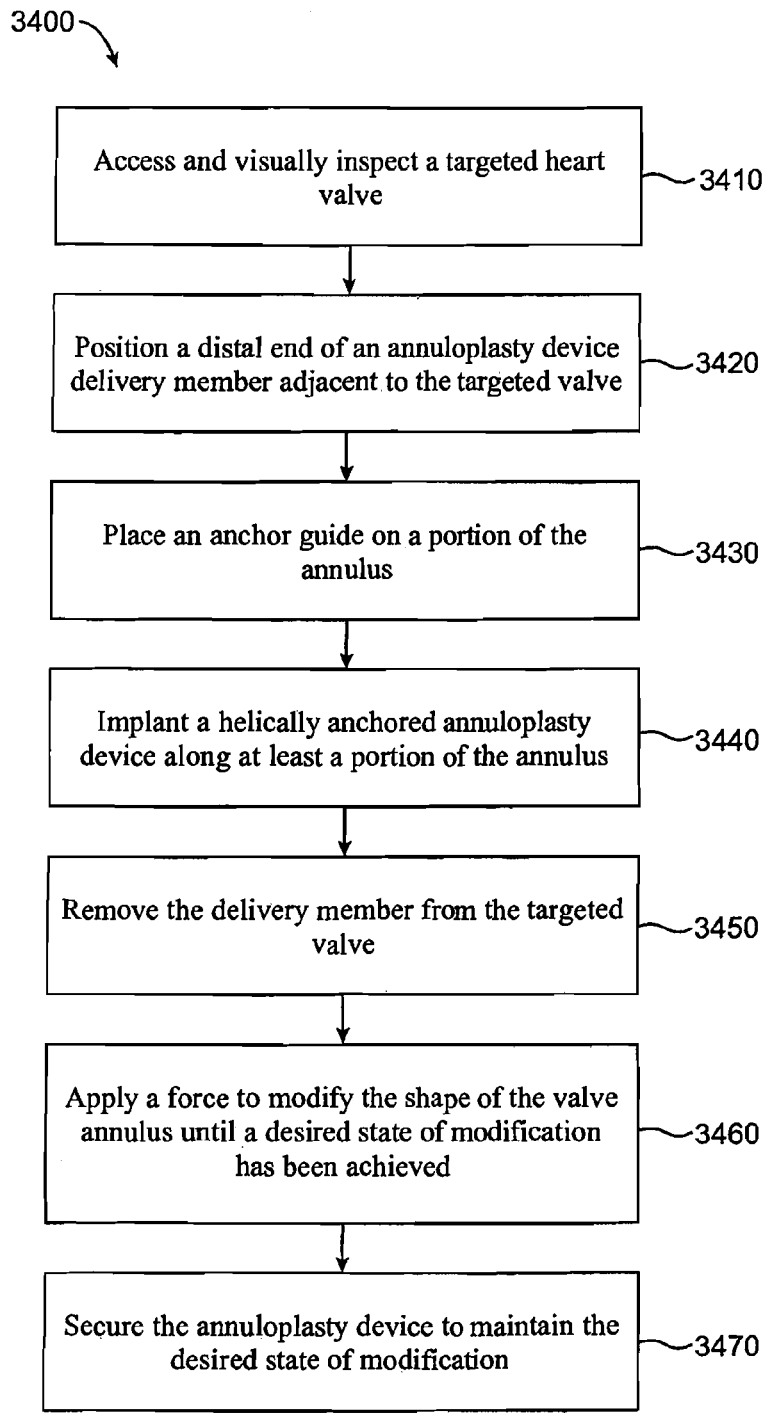
FIG. 38 is a flow chart showing one embodiment of a surgical access based method for implanting a helically helical anchored annuloplasty device according to the current invention

FIG. 38 is a flowchart illustrating one embodiment of a traditional surgical access based method 3400 to modify the shape of valve annulus according to the current invention. To begin the method, a clinical will access and visually inspect a targeted heart valve 3410. Next the distal end of an annuloplasty device delivery member is positioned adjacent to the targeted valve 3420 and the anchor guide is placed on a portion of the annulus 3430. The helically anchored annuloplasty device is then implanted along at least a portion of the annulus 3440 before the delivery member is removed from the targeted valve 3450. A force is applied to modify the shape of the valve annulus until a desired state of modification has been achieved 3460 and the annuloplasty device is secured to maintain the desired state of modification 3470.

While the invention has been described with reference to particular embodiments, it will be understood by one skilled in the art that variations and modifications may be made in form and detail without departing from the spirit and scope of the invention.

The invention claimed is:

1. A system for modifying a heart valve annulus, comprising:
   an elongated, generally tubular delivery member having a delivery lumen, a distal end, and a proximal end;
   an elongated driver having a distal end and a proximal end, the driver being movably inserted into the delivery lumen;
   an anchor guide operatively provided so as to extend from the distal end of the delivery member;
   a helical anchor configured for delivery to and implantation in the annulus of a heart valve, the helical anchor having the same shape for both delivery and implantation;
   the helical anchor having a long axis, a distal end, a proximal end, and a plurality of coils, the proximal end of the helical anchor being releasably connected to the distal end of the driver such that the helical anchor can be rotated by turning the proximal end of the driver;
   the distal end of the helical anchor having a sharpened tip portion configured to pierce tissue of the annulus, allowing the plurality of coils of the helical anchor to embed within the tissue of the annulus as the driver is rotated;
   the coils of the helical anchor defining an inner channel that has a generally cylindrical shape and communicates along the length of the helical anchor;
   an elongated flexible tether having a first end and a second end, and the tether being inserted through at least a portion of the delivery member and through the inner channel along the length of the helical anchor so that the helical anchor can be curved along its long axis by pulling on at least one of the ends of the flexible tether.

2. The system of claim 1 wherein the delivery member further includes a tether lumen extending along at least a portion thereof, the tether lumen having a distal opening located adjacent the distal end of the delivery member and a proximal opening located distal to the proximal end of the delivery member and the tether is insertable into the tether lumen.

3. The system of claim 1 further comprising means for releasably connecting the helical anchor to the distal end of the driver.

4. The system of claim 1 wherein the driver is rotatably and axially movable within the delivery member to drive the helical anchor through a heart valve annulus along the at least one anchor guide.

5. A system for modifying a heart valve annulus, comprising:
   an elongated, generally tubular delivery member having a delivery lumen, a distal end, and a proximal end;
   an elongated driver having a distal end and a proximal end, the driver being movably inserted into the delivery lumen;
   an anchor guide operatively provided so as to extend from the distal end of the delivery member;
   the anchor guide being shaped to match the curvature of at least a portion of a heart valve annulus;
   a helical anchor configured for delivery to and implantation in the annulus of a heart valve, the helical anchor having the same shape for both delivery and implantation;
   the helical anchor having a long axis, a distal end, a proximal end, and a plurality of coils, the proximal end of the at least one helical anchor being releasably connected to the distal end of the driver such that the helical anchor can be rotated by turning the proximal end of the driver and so that the helical anchor can be driven along the shaped curvature of the anchor guide;
   the distal end of the helical anchor having a sharpened tip portion configured to pierce tissue of the annulus, allowing the plurality of coils of the helical anchor to embed within the tissue of the annulus as the driver is rotated;
   the coils of the helical anchor defining an inner channel that has a generally cylindrical shape and communicates along the length of the helical anchor;
   an elongated flexible tether having a first end and a second end, and the tether being inserted to extend at least partially through the system.

6. The system of claim 5 wherein the anchor guide is an extension of the distal end of the delivery member that extends beyond a distal opening of the delivery lumen and the anchor guide can be shaped to match the curvature of at least a portion of a heart valve annulus by manipulating the tether.

7. The system of claim 5 wherein the driver is a generally tubular member with an anchor guide lumen communicating therethrough and the anchor guide is an elongated flexible member that is inserted into the anchor guide lumen;
   the anchor guide having a lumen for receiving the tether; and
   the at least one anchor guide is movable between a delivery position within the guide lumen and a deployment position wherein the at least one anchor guide extends from the distal end of the at least one delivery member.

8. The system of claim 5 wherein the delivery member further includes a tether lumen extending along at least a portion thereof, the tether lumen having a distal opening located adjacent the distal end of the delivery member and a proximal opening located distal to the proximal end of the delivery member and the tether is insertable into the tether lumen.

9. The system of claim 5 wherein a portion of the distal end of the delivery member is movable between a substantially linear insertion configuration and curved delivery configuration.

10. The system of claim 5 wherein the anchor guide portion is a flexible steerable member having a lumen for receiving a tether.

11. The system of claim 5 further comprising a handle mounted on the proximal end of the delivery member, and a torque knob on the proximal end of the driver.

12. The system of claim 5 wherein the driver is rotatably and axially movable within the delivery member to drive the helical anchor through a heart valve annulus along the anchor guide.

13. The system of claim 5 further comprising means for securing the first end and second end of the tether to the at least one helical anchor.

14. The system of claim 13 wherein the means for securing the first end and second end of the tether is at least one stop member that has a size and shape such that it cannot pass through the inner channel of the helical anchor;
   the stop member having at least one tether channel passing therethrough; and the tether further comprising a plurality of locking members spaced along at least a portion thereof.

15. The system of claim 14 wherein the stop member having at least one tether channel is two stop members, each having a single tether channel.

\* \* \* \* \*